United States Patent [19]

Reitz et al.

[11] Patent Number: 5,451,592
[45] Date of Patent: Sep. 19, 1995

[54] METHOD OF USING N-ARYLHETEROARYLALKYL 1-HETEROARYL-IMIDAZOL-2-ONE COMPOUNDS FOR TREATMENT OF A GLAUCOMA DISORDER

[75] Inventors: David B. Reitz, Chesterfield; Robert E. Manning, St. Louis, both of Mo.

[73] Assignee: C.D. Searle & Co., Chicago, Ill.

[21] Appl. No.: 960,603

[22] Filed: Oct. 13, 1992

Related U.S. Application Data

[63] Continuation-in-part of Ser. No. 681,011, Apr. 5, 1991, Pat. No. 5,164,403.

[51] Int. Cl.⁶ ............................................. A61K 31/44
[52] U.S. Cl. ..................................... 514/340; 514/341
[58] Field of Search ................. 546/778; 514/341, 340

[56] References Cited

U.S. PATENT DOCUMENTS

| | | | |
|---|---|---|---|
| 3,857,845 | 12/1974 | Palazzo | 260/268 |
| 4,294,972 | 1/1979 | Cassidy et al. | 548/264 |
| 4,816,463 | 3/1989 | Blankley et al. | 514/293 |
| 4,880,804 | 11/1989 | Carini et al. | 514/234.5 |

FOREIGN PATENT DOCUMENTS

| | | |
|---|---|---|
| 621842 | 2/1963 | Belgium . |
| 253310 | 1/1988 | European Pat. Off. ... C07D 403/14 |
| 283310 | 9/1988 | European Pat. Off. ... C07D 295/04 |
| 323841 | 7/1989 | European Pat. Off. ... C07D 403/10 |
| 508393 | 10/1992 | European Pat. Off. ... C07D 401/14 |
| 160447 | 8/1981 | German Dem. Rep. ... A01N 43/64 |
| 92/07834 | 5/1992 | WIPO ........................ C07D 233/70 |

OTHER PUBLICATIONS

P. C. Wong et al., *J. Pharmacol. Exp. Ther.*, 247(1), 1–7 (1988).

A. T. Chiu et al., *European J. Pharmacol.*, 157, 13–21 (1988).

A. T. Chiu et al., *J. Pharmacol. Exp. Ther.*, 250(3), 867–874 (1989).

*Primary Examiner*—C. Warren Ivy
*Assistant Examiner*—Raymond Covington
*Attorney, Agent, or Firm*—J. Timothy Keane

[57] ABSTRACT

A class of N-arylheteroarylalkyl 1-heteroaryl-imidazol-2-one compounds is described for use in treatment of glaucoma disorder. Compounds of particular interest are angiotensin II antagonists of the formula

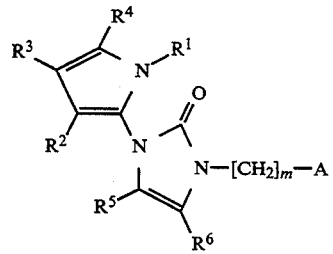

wherein A is selected from

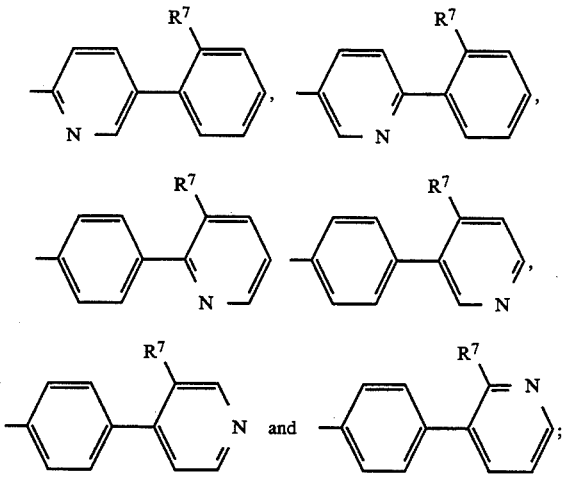

wherein $R^1$ is selected from hydrido and alkyl; wherein each of $R^2$, $R^3$ and $R^4$ is independently selected from hydrido, alkyl, alkoxy, halo, hydroxy, carboxyl, alkoxycarbonyl, formyl and acetyl; wherein $R^5$ is hydrido; wherein $R^6$ is alkyl; wherein $R^7$ is an acidic group selected from COOH and

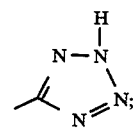

or a stereoisomer or a tautomer thereof or a pharmaceutically-acceptable salt thereof.

6 Claims, No Drawings

METHOD OF USING N-ARYLHETEROARYLALKYL 1-HETEROARYL-IMIDAZOL-2-ONE COMPOUNDS FOR TREATMENT OF A GLAUCOMA DISORDER

RELATED APPLICATION

This is a continuation-in-part of U.S. application Ser. No. PCT/US92/02439 filed Apr. 1, 1992 which is a continuation-in-part of U.S. application Ser. No. 07/681,011 filed Apr. 5, 1991, now U.S. Pat. No. 5,164,403.

FIELD OF THE INVENTION

Non-peptidic N-arylheteroarylalkyl imidazol-2-one compounds are described for use in treatment of circulatory disorders such as hypertension and congestive heart failure. Of particular interest are angiotensin II antagonist compounds provided by a 1-heteroaryl-imidazol-2-one having an arylheteroarylmethyl moiety attached to the 3-nitrogen atom of the 1-heteroaryl-imidazol-2-one.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, J. Pharmacol. Exp. Ther., 247(1), 1–7 (1988)]. Also, the sodium salt of 2-butyl-4-chloro-1-(2-nitrobenzyl) imidazole-5-acetic acid has specific competitive angiotensin II antagonist activity as shown in a series of binding experiments, functional assays and in vivo tests [A. T. Chiu et al, European J. Pharmacol., 157, 13–21 (1988)]. A family of 1-benzylimidazole-5-acetate derivatives has been shown to have competitive angiotensin II antagonist properties [A. T. Chiu et al, J. Pharmacol. Exp. Ther., 250(3), 867–874 (1989)]. U.S. Pat. No. 4,816,463 to Blankey et al describes a family of 4,5,6,7-tetrahydro-1H-imidazo(4,5-c)tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published Jan. 20, 1988, describes a series of aralkyl imidazole compounds, including in particular a family of biphenylmethyl substituted imidazoles, as antagonists to the angiotensin II receptor. EP No. 323,841 published Jul. 12, 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on a triazole ring. For example, East German Patent No. 160,447 published Aug. 3, 1983 describes a family of 1,2,4-triazolin-5-one compounds, specifically 2,4-dihydro-4,5-bis(phenylmethyl)-3H-1,2,4-triazol-3-one, for use as herbicides. Belgian Patent No. 806,146 published Oct. 16, 1972 describes a family of triazolinone compounds, including the compound (3-(4-m-chlorophenyl-1-piperazinyl)-propyl)-3,4-diethyl-1,2,4-triazolin-5-one, having tranquilizer, hypotensive and analgesic activities. Belgian Patent No. 631,842 published Feb. 28, 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published Jun. 15, 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published Mar. 18, 1987 describes a family of N¹-diarylmethyl-N²-aminoalkyl-diaza-heterocyclic derivatives for treating cerebral vascular and ischemic diseases and for protecting against anoxia.

DESCRIPTION OF THE INVENTION

A class of N-substituted arylheteroarylalkyl 1-heteroaryl-imidazol-2-one compounds useful in treating circulatory disorders, particularly cardiovascular disorders, is defined by Formula I:

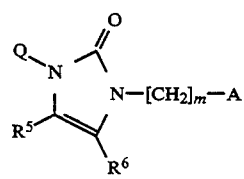

wherein Q is a heterocyclic group having five ring-member atoms, which ring-member atoms are selected from carbon atoms and nitrogen atoms, with the requirement that at least one ring-member atom be a carbon atom and at least one ring member atom be a nitrogen atom, which heterocyclic group is fully unsaturated and wherein said heterocyclic group may be substituted on one or more substitutable positions by one or more groups independently selected from hydrido, alkyl, alkoxy, cyano, halo, hydroxy, nitro, amino, alkylamino, carboxyl, alkoxycarbonyl, formyl, oxo, alkylcarbonyl and haloalkylcarbonyl; wherein $R^5$ is selected from hydrido, alkyl, halo, haloalkyl, formyl, carboxyl and alkoxyalkyl; wherein $R^6$ is selected from alkyl, phenyl, phenylalkyl, cycloalkyl and cycloalkylalkyl; wherein A is an acid-group-substituted pyridinyl-phenyl moiety selected from

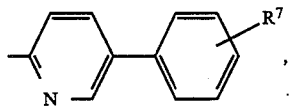

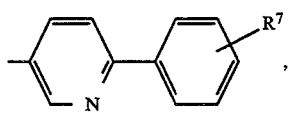

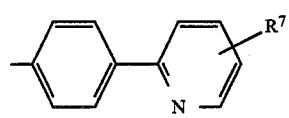

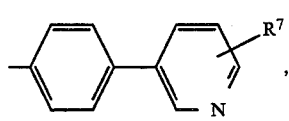

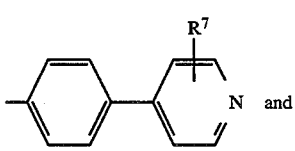

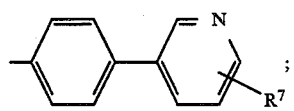

wherein m is a number selected from one to four, inclusive; wherein $R^5$ is an acidic group selected from COOH and

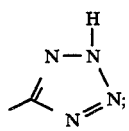

or a stereoisomer or a tautomer thereof or a pharmaceutically-acceptable salt thereof.

Regioisomers of compounds of Formula I are also embraced as part of the invention, particularly those regioisomers formed by various substitutions on nitrogen atoms of the imidazole ring relative to substitutions on the carbon atoms of the imidazole ring. For purposes of nomenclature, a numbering system for the imidazole ring is shown below for a preferred set of compounds of the invention within Formula I:

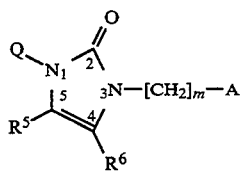

wherein each of Q, $R^5$, $R^6$, m and A is as defined above.

Compounds of Formula I would be useful in treating a variety of circulatory disorders and circulatory-related disorders, including cardiovascular disorders, such as hypertension, congestive heart failure and arteriosclerosis, and other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

Examples of heteroaryl groups embraced by the Q group are the following moieties:

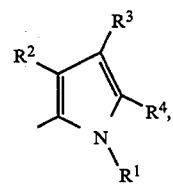

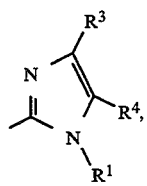

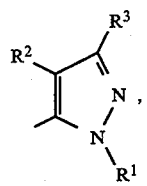

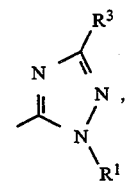

-continued

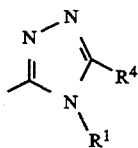

and

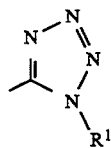

wherein R¹ is selected from hydrido and alkyl; wherein each R², R³ and R⁴ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl.

Within the compounds of Formula I there is a first group of compounds of more interest as represented by Formula II:

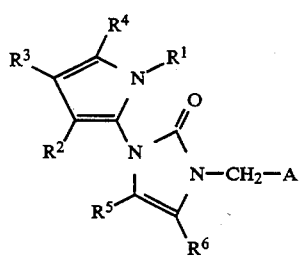

wherein R¹ is selected from hydrido and alkyl; wherein each R², R³ and R⁴ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein R⁵ is selected from hydrido, methyl, fluoro, chloro, monofluoromethyl, difluoromethyl, trifluoromethyl, formyl, carboxyl and dimethoxymethyl; wherein R⁶ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

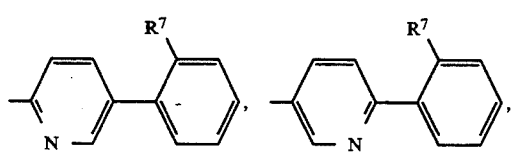

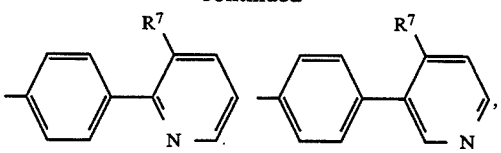

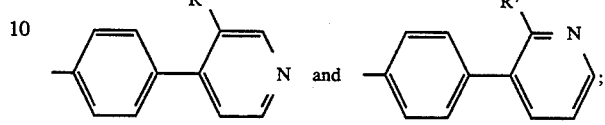

wherein R⁷ is an acidic group selected from COOH and

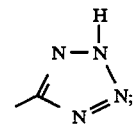

or a stereoisomer or a tautomer thereof or a pharmaceutically-acceptable salt thereof.

Within this first group of compounds of Formula II there is a first class of higher-interest compounds of Formula II (a):

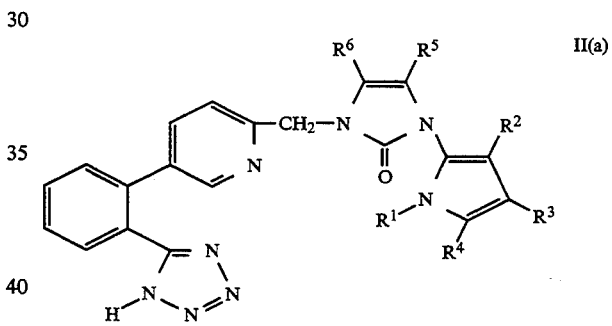

wherein R¹ is selected from hydrido, methyl, ethyl, n-propyl, isopropyl, n-butyl, tert-butyl, sec-butyl, isobutyl and n-pentyl; wherein R², R³ and R⁴ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II(a) consists of compounds and their stereoisomers and tautomers and the pharmaceutically-acceptable salts thereof, said compounds consisting of 1-(1-methyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-ethyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-propyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-isopropyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-butyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-secbutyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-isobutyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-tertbutyl-1H-pyrrol-2-yl)-4-propyl-1,3-dihydro-3-[[5-[2-(1H-tetrazol-5-yl)phenyl]-2-pyridinyl]methyl]-2H-imidazol-2-one;

1-(1-methyl-1H-pyrrol-2-yl)-4-butyl-1,3-dihydro-3-[[5-[2-(1H-tetrazol-5-yl)phenyl]-2-pyridinyl]methyl]-2H-imidazol -2-one;

1-(1-ethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-1H-pyrrol-2-yl)-4-butyl-1,3-dihydro-3-[[5-[2-(1H- tetrazol-5-yl)phenyl]-2-pyridinyl]methyl]-2H-imidazol-2-one;

1-(1-butyl -1H-pyrrol-2-yl)-4-butyl -1,3-dihydro-3-[[5-[2-(1H-tetrazol-5-yl)phenyl]-2-pyridinyl]methyl]-2H-imidazol-2-one;

1-(1-secbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isobutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-tertbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1,3-dimethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-ethyl -1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-propyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-isopropyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-trifluoromethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-hydroxymethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-carbomethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-carboxy-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3-acetyl-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3-trifluoroacetyl-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3-chloro-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3-formyl-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3-bromo-1H-pyrrol-2-yl)-4-butyl-1,3-dihydro-3-[[5-[2-(1H-tetrazol-5-yl) phenyl]-2-pyridinyl]methyl]-2H-imidazol-2-one;

1-(1-methyl-3- fluoro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-cyano-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-carboethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-methyl-3-tertbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-methyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1,3-diethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-propyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-isopropyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-trifluoromethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-hydroxymethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-carbomethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-carboxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-acetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-trifluoroacetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-chloro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-formyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

-(1-ethyl-3-bromo-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3- fluoro-1H-pyrrol-2-yl-4-butyl-1,3-dihydro-3-[[5-[2-(1H-tetrazol-5-yl)phenyl]-2-pyridinyl]methyl]-2H-imidazol-2-one;

1-(1-ethyl-3-cyano-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-carboethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-ethyl-3-tertbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-methyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-ethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1,3-dipropyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-isopropyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-trifluoromethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-hydroxymethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-carbomethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-carboxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-acetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-trifluoroacetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-chloro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-formyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-bromo-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-fluoro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-cyano-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-carboethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-propyl-3-tertbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-methyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-ethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-propyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1,3-diisopropyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-trifluoromethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-hydroxymethyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-carbomethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-carboxy-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-acetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-trifluoroacetyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-chloro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-formyl-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-bromo-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-fluoro-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-cyano-1H-pyrrol-2-yl)-4-butyl-1,3-dihydro-3-[[5-[2-(1H-tetrazol-5-yl)phenyl]-2-pyridinyl]methyl]-2H-imidazol-2-one;

1-(1-isopropyl-3-carboethoxy-1H-pyrrol-2-yl)-4-butyl-1,3-dihydro-3-[[5-[2-(1H-tetrazol-5-yl)phenyl]-2-pyridinyl]methyl]-2H-imidazol-2-one and 1-(1-isopropyl-3-tertbutyl-1H-pyrrol-2-yl)-4-butyl-1,3-dihydro-3-[[5-[2-(1H-tetrazol-5-yl)phenyl]-2-pyridinyl]methyl]-2H-imidazol-2-one.

Within this first group of compounds of Formula II there is a second class of higher-interest compounds of Formula II (b):

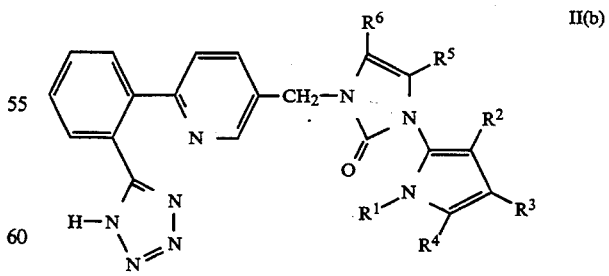

wherein $R^1$ is selected from hydrido, methyl, ethyl, n-propyl, isopropyl, n-butyl, tert-butyl, sec-butyl, isobutyl and n-pentyl; wherein $R^2$, $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II (b) consists of compounds and their stereoisomers and tautomers and the pharmaceutically-acceptable salts thereof, said compounds consisting of 1-(1-methyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-ethyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-propyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-isopropyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-butyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-secbutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-isobutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-tertbutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-1H-pyrrol-2-yl)-4-butyl-1,3-dihydro-3-[[6-[2-(1H-tetrazol-5-yl)phenyl]-3-pyridinyl]methyl]-2H-imidazol-2- one;

1-(1-propyl-1H-pyrrol-2-yl)-4-butyl-1,3-dihydro-3-[[6-[2-(1H-tetrazol-5-yl)phenyl]-3-pyridinyl]methyl]-2H-imidazol-2- one;

1-(1-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-butyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-secbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isobutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-dimethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3- acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carboethoxy-1H-pyrrol-2-yl)-4-butyl-1,3-dihydro-3-[[6-[2-(1H-tetrazol-5-yl)phenyl]-3-pyridinyl]methyl]-2 H-imidazol-2-one;

1-(1-methyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-diethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-dipropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-trifluoromethyl-1H-pyrrol-2-yl)-4-butyl-1,3-dihydro-3-[[6-[2-(1H-tetrazol-5-yl)phenyl]-3-pyridinyl]methyl]-2 H-imidazol-2-one;

1-(1-propyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-carbomethoxy-1H-pyrrol-2-yl)-4-butyl-1,3-dihydro-3-[[6-[2-(1H-tetrazol-5-yl)phenyl]-3-pyridinyl]methyl]-2 H-imidazol-2-one;

1-(1-propyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-carboethoxy-1H-pyrrol-2-yl)-4-butyl-1,3-dihydro-3-[[6-[2-(1H-tetrazol-5-yl)phenyl]-3-pyridinyl]methyl]-2 H-imidazol-2-one;

1-(1-propyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-diisopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one and 1-(1-isopropyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one.

Within this first group of compounds of Formula II there is a third class of higher-interest compounds of Formula II(c):

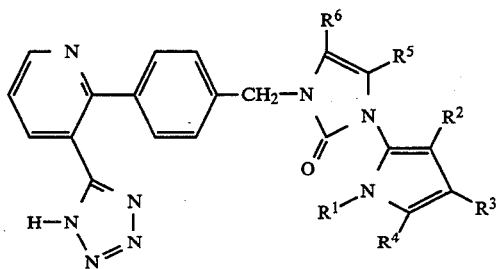

II(c)

wherein R¹ is selected from hydrido, methyl, ethyl, n-propyl, isopropyl, n-butyl, tert-butyl, sec-butyl, isobutyl and n-pentyl; wherein R², R³ and R⁴ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II(c) consists of compounds and their stereoisomers and tautomers and the pharmaceutically-acceptable salts thereof, said compounds consisting of 1-(1-methyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-ethyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-propyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-isopropyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-butyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-secbutyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-isobutyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-tertbutyl-1H-pyrrol-2-yl)-4-propyl-1,3-dihydro-3-[[4-[3-(1H-tetrazol-5-yl)phenyl]-2-pyridinyl]methyl]-2H-imidazol-2-one;

1-(1-methyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-butyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-secbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isobutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-tertbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1,3-dimethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-ethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-propyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-isopropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-trifluoromethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-hydroxymethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-carbomethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-carboxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-acetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-trifluoroacetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-chloro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-formyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-bromo-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-fluoro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-cyano-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-carboethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-methyl-3-tertbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-methyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1,3-diethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-propyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-isopropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-trifluoromethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-hydroxymethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-carbomethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-carboxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-acetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-trifluoroacetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-chloro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-formyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-bromo-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-fluoro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-cyano-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-carboethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-3-tertbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-methyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-ethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1,3-dipropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-isopropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-trifluoromethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-hydroxymethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-carbomethoxy-1H-pyrrol-2-yl)-4-butyl-1,3-dihydro-3-[[4-[3-(1H-tetrazol-5-yl)phenyl]-2-pyridinyl]methyl]-2 H-imidazol-2-one;

1-(1-propyl-3-carboxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-acetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-trifluoroacetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-chloro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-formyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-bromo-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-fluoro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-cyano-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-propyl-3-carboethoxy-1H-pyrrol-2-yl)-4-butyl-1,3-dihydro-3-[[4-[3-(1H-tetrazol-5-yl)phenyl]-2-pyridinyl]methyl]-2 H-imidazol-2-one;

1-(1-propyl-3-tertbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-methyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-ethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-propyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1,3-diisopropyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-trifluoromethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-hydroxymethyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-carbomethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-carboxy-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-acetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-trifluoroacetyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-chloro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-formyl-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-bromo-1H-pyrrol-2-yl)-4-butyl-1,3-[[4-[3-(1H-tetrazol-5-yl)phenyl]-2-pyridinyl]methyl]-2H-imidazol-2-one;

1-(1-isopropyl-3-fluoro-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-cyano-1H-pyrrol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-3-carboethoxy-1H-pyrrol-2-yl)-4-butyl-1,3-dihydro-3-[[4-[3-(1H-tetrazol-5-yl)phenyl]-2-pyridinyl]methyl]-2H-imidazol-2-one and 1-(1-isopropyl-3-tertbutyl-1H-pyrrol-2-yl)-4-butyl-1,3-dihydro-3-[[4-[3-(1H-tetrazol-5-yl)phenyl]-2-pyridinyl]methyl]-2H-imidazol-2-one.

Within this first group of compounds of Formula II there is a fourth class of higher-interest compounds of Formula II(d):

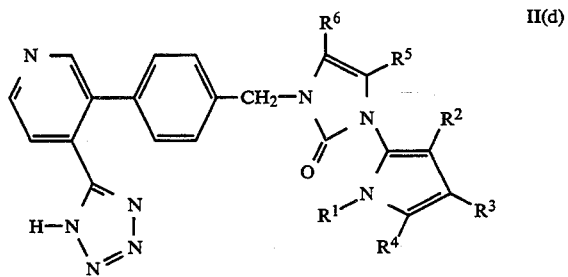

wherein $R^1$ is selected from hydrido, methyl, ethyl, n-propyl, isopropyl, n-butyl, tert-butyl, sec-butyl, isobutyl and n-pentyl; wherein $R^2$, $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II (d) consists of compounds and their stereoisomers and tautomers and the pharmaceutically-acceptable salts thereof, said compounds consisting of 1-(1-methyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-ethyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-propyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-isopropyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-butyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-secbutyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-isobutyl-1H-pyrrol-2-yl)-4-propyl-1,3-dihydro-3-[[4-[4-(1H-tetrazol-5-yl)phenyl]-3-pyridinyl]methyl]-2 H-imidazol-2-one;

1-(1-tertbutyl-1H-pyrrol-2-yl)-4-propyl-1,3-dihydro-3-[[4-[4-(1H-tetrazol-5-yl)phenyl]-3-pyridinyl]methyl]-2H-imidazol-2-one;

1-(1-methyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-butyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-secbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isobutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-tertbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1,3-dimethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-ethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-propyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-isopropyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-trifluoromethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-hydroxymethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-carbomethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-carboxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-acetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-trifluoroacetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-chloro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-formyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-bromo-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-fluoro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-cyano-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-carboethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-methyl-3-tertbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-methyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1,3-diethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-propyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-isopropyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-trifluoromethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-hydroxymethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-carbomethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-carboxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-acetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-trifluoroacetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-chloro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-formyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-bromo-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-fluoro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-cyano-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-carboethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-3-tertbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-methyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-ethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1,3-dipropyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-isopropyl-1H-pyrrol-2-yl)-4-butyl-1,3-dihydro-3-[[4-[4-(1H-tetrazol-5-yl) phenyl]-3-pyridinyl]methyl]-2H-imidazol-2-one;

1-(1-propyl-3-trifluoromethyl-1 H-pyrrol-2-yl)-4-butyl-1,3-dihydro-3-[[4-[4-(1H-tetrazol-5-yl) phenyl]-3-pyridinyl]methyl]-2H-imidazol-2-one;

1-(1-propyl-3-hydroxymethyl-1H-pyrrol-2-yl)-4-butyl-1,3-dihydro-3-[[4-[4-(1H-tetrazol-5-yl) phenyl]-3-pyridinyl]methyl]-2H-imidazol-2-one;

1-(1-propyl-3-carbomethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-carboxy-1H-pyrrol-2-yl)-4-butyl-1,3-d[[4-[4-(1H-tetrazol-5-yl)phenyl]-3-pyridinyl]methyl]-2H-imidazol-2-one;

1-(1-propyl-3-acetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-trifluoroacetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-chloro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-formyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-bromo-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-fluoro-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-cyano-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-carboethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-propyl-3-tertbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-3-methyl-1H-pyrrol-2-yl)-4-butyl-1,3-dihydro-3-[[4-[4-(1H-tetrazol-5-yl) phenyl]-3-pyridinyl]methyl]-2H-imidazol-2-one;

1-(1-isopropyl-3-ethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-3-propyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1,3-diisopropyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-3-trifluoromethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-3-hydroxymethyl-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-carbomethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-carboxy-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-acetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-trifluoroacetyl-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-chloro-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-formyl-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-bromo-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-fluoro-1H-pyrrol-2-yl)-4-butyl-1,3-dihydro-3-[[4-[4-(1H-tetrazol-5-yl)phenyl]-3-pyridinyl]methyl]-2H-imidazol-2-one
1-(1-isopropyl-3-cyano-1H-pyrrol-2-yl)-4-butyl-1,3-dihydro-3-[[4-[4-(1H-tetrazol-5-yl)phenyl]-3-pyridinyl]methyl]-2H-imidazol-2-one;
1-(1-isopropyl-3-carboethoxy-1H-pyrrol-2-yl)-4-butyl-1,3-dihydro-3-[[4-[4-(1H-tetrazol-5-yl)phenyl]-3-pyridinyl]methyl]-2H-imidazol-2-one and
1-(1-isopropyl-3-tertbutyl-1H-pyrrol-2-yl)-4-butyl-1,3-dihydro-3-[[4-[4-(1H-tetrazol-5-yl)phenyl]-3-pyridinyl]methyl]-2H-imidazol-2-one.

Within this first group of compounds of Formula II there is a fifth class of higher-interest compounds of Formula II(e):

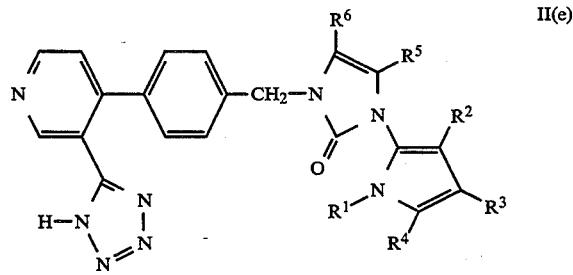

II(e)

wherein $R^1$ is selected from hydrido, methyl, ethyl, n-propyl, isopropyl, n-butyl, tert-butyl, sec-butyl, isobutyl and n-pentyl; wherein $R^2$, $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II(e) consists of compounds and their stereoisomers and tautomers and the pharmaceutically-acceptable salts thereof, said compounds consisting of 1-(1-methyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-ethyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-propyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-isopropyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-butyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-secbutyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-isobutyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-tertbutyl-1H-pyrrol-2-yl)-4-propyl-1,3-dihydro-3-[[4-[3-(1H-tetrazol-5-yl)phenyl]-4-pyridinyl]methyl]-2H-imidazol-2-one;
1-(1-methyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-ethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-propyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-isopropyl-1H-pyrrol-2-yl)-4-butyl-1,3-dihydro-3-[[4-[3-(1H-tetrazol-5-yl) phenyl]-4-pyridinyl]methyl]-2H-imidazol-2-one;
1-(1-butyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-secbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-isobutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-tertbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1,3-dimethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-methyl-3-ethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-methyl-3-propyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-methyl-3-isopropyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-methyl-3-trifluoromethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;
1-(1-methyl-3-hydroxymethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-carbomethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-carboxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-acetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-trifluoroacetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-chloro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-formyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-bromo-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-fluoro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-cyano-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-carboethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-methyl-3-tertbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-methyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1,3-diethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-propyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-isopropyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-trifluoromethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-hydroxymethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-carbomethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-carboxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-acetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-trifluoroacetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-chloro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-formyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-bromo-1H-pyrrol-2-yl)-4-butyl-1,3-dihydro-3-[[4-3-(1H-tetrazol-5-yl)phenyl]-4-pyridinyl]methyl]-2H-imidazol-2-one;

1-(1-ethyl-3-fluoro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-cyano-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-carboethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-3-tertbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-methyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-ethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1,3-dipropyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-isopropyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-trifluoromethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-hydroxymethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-carbomethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-carboxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-acetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-trifluoroacetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-chloro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-formyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-bromo-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-fluoro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-cyano-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-propyl-3-carboethoxy-1H-pyrrol-2-yl)-4-butyl-1,3-dihydro-3-[[4-[3-(1H-tetrazol-5-yl)phenyl]-4-pyridinyl]methyl]-2 H-imidazol-2-one;

1-(1-propyl-3-tertbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-methyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-ethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-propyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1,3-diisopropyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-trifluoromethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-hydroxymethyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-carbomethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-carboxy-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-acetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-trifluoroacetyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-chloro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-formyl-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-bromo-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-fluoro-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-cyano-1H-pyrrol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-3-carboethoxy-1H-pyrrol-2-yl)-4-butyl-1,3-dihydro-3-[[4-[3-(1H-tetrazol-5-yl)phenyl]-4-pyridinyl]methyl]-2H-imidazol-2-one and 1-(1-isopropyl-3-tertbutyl-1H-pyrrol-2-yl)-4-butyl-1,3-dihydro-3-[[4-[3-(1H-tetrazol-5-yl)phenyl]-4-pyridinyl]methyl]-2H-imidazol-2-one.

Within this first-group of compounds of Formula II there is a sixth class of higher-interest compounds of Formula II(f):

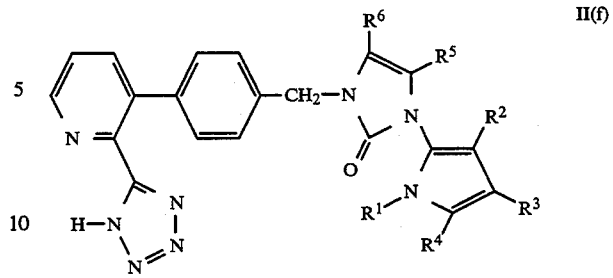

wherein $R^1$ is selected from hydrido, methyl, ethyl, n-propyl, isopropyl, n-butyl, tert-butyl, sec-butyl, isobutyl and n-pentyl; wherein $R^2$, $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula II (f) consists of compounds and their stereoisomers and tautomers and the pharmaceutically-acceptable salts thereof, said compounds consisting of
1-(1-methyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-ethyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-propyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-isopropyl-1H-pyrrol-2-yl)-4-propyl-1,3-dihydro-3-(1H-tetrazol-5-yl)phenyl]-3-pyridinyl]methyl]-2H-imidazol-2-one;

1-(1-butyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-secbutyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-isobutyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-tertbutyl-1H-pyrrol-2-yl)-4-propyl-1,3-dihydro-3-[[4-[2-(1H-tetrazol-5-yl)phenyl]-3-pyridinyl]methyl]-2H-imidazol-2-one;

1-(1-methyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-butyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-secbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isobutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-tertbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1,3-dimethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-ethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-propyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-isopropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-trifluoromethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-hydroxymethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-carbomethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-carboxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-acetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-trifluoroacetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-chloro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-formyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-bromo-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-fluoro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-cyano-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-carboethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-methyl-3-tertbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-methyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1,3-diethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-propyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-isopropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-trifluoromethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-hydroxymethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-carbomethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-carboxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-acetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-trifluoroacetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-chloro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-formyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-bromo-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-fluoro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-cyano-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-carboethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-3-tertbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-methyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-ethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1,3-dipropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-isopropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-trifluoromethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-hydroxymethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-carbomethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-carboxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-acetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-trifluoroacetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-chloro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-formyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-bromo-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-fluoro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-cyano-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-carboethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-propyl-3-tertbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-methyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-ethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-propyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1,3-diisopropyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-trifluoromethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-hydroxymethyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-carbomethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-carboxy-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-acetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-trifluoroacetyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-chloro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-formyl-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-bromo-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-fluoro-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-cyano-1H-pyrrol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-3-carboethoxy-1H-pyrrol-2-yl)-4-butyl-1,3-dihydro-3-[[4-[2-(1H-tetrazol-5-yl)phenyl]-3-pyridinyl]methyl]-2H-imidazol-2-one and 1-(1-isopropyl-3-tertbutyl-1H-pyrrol-2-yl)-4-butyl-1,3-dihydro-3-[[4-[2-(1H-tetrazol-5-yl)phenyl]-3-pyridinyl]methyl]-2H-imidazol-2-one.

Within the compounds of Formula I there is a second group of compounds of more interest as represented by Formula III:

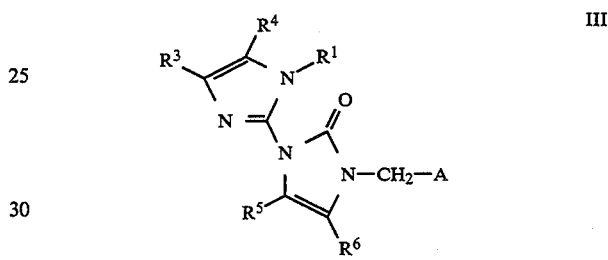

wherein $R^1$ is selected from hydrido and alkyl; wherein each of $R^3$ and $R^4$ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

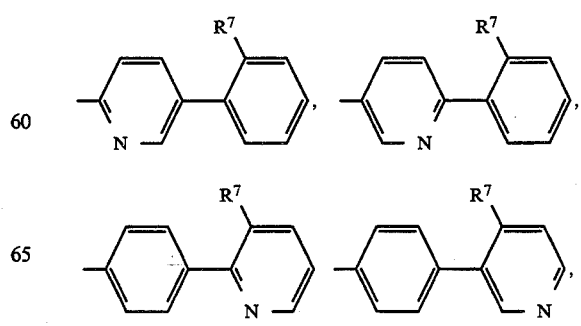

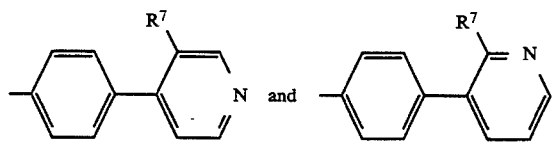

wherein R⁷ is an acidic group selected from COOH and

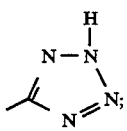

or a stereoisomer or a tautomer thereof or a pharmaceutically-acceptable salt thereof.

Within this second group of compounds of Formula III there is a first class of higher-interest compounds of Formula III(a):

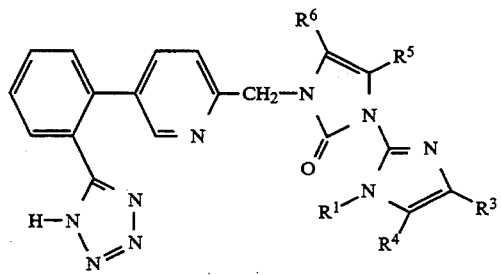

wherein $R^1$ is selected from hydrido, methyl, ethyl, n-propyl, isopropyl, n-butyl, tert-butyl, sec-butyl, isobutyl and n-pentyl; wherein each of $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(a) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-ethyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-propyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-isopropyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-butyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-secbutyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-isobutyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-tertbutyl-1H-imidazol-2-yl)-4-propyl-1,3-dihydro-3-[[5-[2-(1H-tetrazol-5-yl)phenyl]-2-pyridinyl]methyl]-2H-imidazol-2-one;
1-(1-methyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-ethyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-propyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-isopropyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-butyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-secbutyl-1H-imidazol-2-yl)-4-butyl-1,3-dihydro-3-[[5-[2-(1H-tetrazol-5-yl)phenyl]-2-pyridinyl]methyl]-2H-imidazol-2-one;
1-(1-isobutyl-1H-imidazol-2-yl)-4-butyl-1,3-dihydro-3-[[5-[2-(1H-tetrazol-5-yl)phenyl]-2-pyridinyl]methyl]-2H-imidazol-2-one and
1-(1-tertbutyl-1H-imidazol-2-yl)-4-butyl-1,3-dihydro-3-[[5-[2-(1H-tetrazol-5-yl)phenyl]-2-pyridinyl]methyl]-2H-imidazol-2-one.

Within this second group of compounds of Formula III there is a second class of higher-interest compounds of Formula III(b):

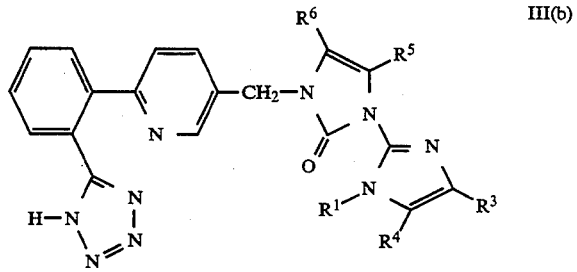

wherein $R^1$ is selected from hydrido, methyl, ethyl, n-propyl, isopropyl, n-butyl, tert-butyl, sec-butyl, isobutyl and n-pentyl; wherein each of $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(b) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-ethyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-propyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-isopropyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-butyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-secbutyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-isobutyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-tertbutyl-1H-imidazol-2-yl)-4-propyl-1,3-dihydro-3-[[6-[2-(1H-tetrazol-5-yl)phenyl]-3-pyridinyl]methyl]-2H-imidazol-2-one;

1-(1-methyl-ill-imidazol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-1H-imidazol-2-yl)-4-butyl-1,3-dihydro-3-[[6-[2-(1H-tetrazol-5-yl)phenyl]-3-pyridinyl]methyl]-2H-imidazol-2-one;

1-(1-propyl-1H-imidazol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-1H-imidazol-2-yl)-4-butyl-1,3-dihydro-3-[[6-[2-(1H-tetrazol-5-yl)phenyl]-3-pyridinyl]methyl]-2H-imidazol-2-one;

1-(1-butyl-1H-imidazol-2-yl)-4-butyl-1,3-dihydro-3-[[6-[2-(1H-tetrazol-5-yl)phenyl]-3-pyridinyl]methyl]-2H-imidazol-2-one;

1-(1-secbutyl-1H-imidazol-2-yl)-4-butyl-1,3-dihydro-3-[[6-[2-(1H-tetrazol-5-yl)phenyl]-3-pyridinyl]methyl]-2H-imidazol-2-one;

1-(1-isobutyl-1H-imidazol-2-yl)-4-butyl-1,3-dihydro-3-[[6-[2-(1H-tetrazol-5-yl)phenyl]-3-pyridinyl]methyl]-2H-imidazol-2-one and 1-(1-tertbutyl-1H-imidazol-2-yl)-4-butyl-1,3-dihydro-3-[[6-[2-(1H-tetrazol-5-yl)phenyl]-3-pyridinyl]methyl]-2H-imidazol-2-one.

Within this second group of compounds of Formula III there is a third class of higher-interest compounds of Formula III(c):

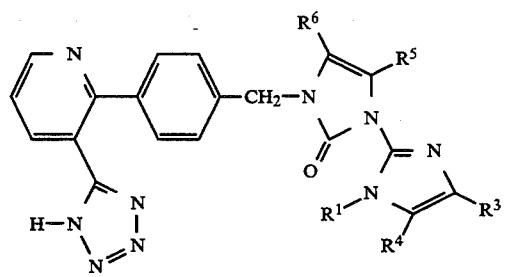

III(c)

wherein $R^1$ is selected from hydrido, methyl, ethyl, n-propyl, isopropyl, n-butyl, tert-butyl, sec-butyl, isobutyl and n-pentyl; wherein each of $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(c) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-ethyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-propyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-isopropyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-butyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-secbutyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-isobutyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-tertbutyl-1H-imidazol-2-yl)-4-propyl-1,3-dihydro-3-[[4-[3-(1H-tetrazol-5-yl)phenyl]-2-pyridinyl]methyl]-2H-imidazol-2-one;

1-(1-methyl-ill-imidazol-2-yl)-4-butyl-1,3-dihydro-3-[[4-[3-(1H-tetrazol-5-yl)phenyl]-2-pyridinyl]methyl]-2H-imidazol-2-one;

1-(1-ethyl-1H-imidazol-2-yl)-4-butyl-1,3-dihydro-3-[[4-[3-(1H-tetrazol-5-yl)phenyl]-2-pyridinyl]methyl]-2H-imidazol-2-one;

1-(1-propyl-1H-imidazol-2-yl)-4-butyl-1,3-dihydro-3-[[4-[3-(1H-tetrazol-5-yl)phenyl]-2-pyridinyl]methyl]-2H-imidazol-2-one;

1-(1-isopropyl-1H-imidazol-2-yl)-4-butyl-1,3-dihydro-3-[[4-[3-(1H-tetrazol-5-yl)phenyl]-2-pyridinyl]methyl]-2H-imidazol-2-one;

1-(1-butyl-1H-imidazol-2-yl)-4-butyl-1, 3-dihydro-3-[[4-[3-(1H-tetrazol-5-yl)phenyl]-2-pyridinyl]methyl]-2H-imidazol-2-one;

1-(1-secbutyl-1H-imidazol-2-yl)-4-butyl-1,3-dihydro-3-[[4-[3-(1H-tetrazol-5-yl)phenyl]-2-pyridinyl]methyl]-2H-imidazol-2-one;

1-(1-isobutyl-1H-imidazol-2-yl)-4-butyl-1,3-dihydro-3-[[4-[3-(1H-tetrazol-5-yl)phenyl]-2-pyridinyl]methyl]-2H-imidazol-2-one and 1-(1-tertbutyl-1H-imidazol-2-yl)-4-butyl-1,3-dihydro-3-[[4-[3-(1H-tetrazol-5-yl)phenyl]-2-pyridinyl]methyl]-2H-imidazol-2-one.

Within this second group of compounds of Formula III there is a fourth class of higher-interest compounds of Formula III(d):

III(d)

wherein R¹ is selected from hydrido, methyl, ethyl, n-propyl, isopropyl, n-butyl, tert-butyl, sec-butyl, isobutyl and n-pentyl; wherein each of R³ and R⁴ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(d) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-ethyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-propyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-isopropyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-butyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-secbutyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-isobutyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-tertbutyl-1H-imidazol-2-yl)-4-propyl-1,3-dihydro-3-[[4-[4-(1H-tetrazol-5-yl)phenyl]-3-pyridinyl]methyl]-2H-imidazol-2-one;

1-(1-methyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-ethyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-propyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-isopropyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-butyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-secbutyl-1H-imidazol-2-yl)-4-butyl-1,3-dihydro-3-[[4-[4-(1H-tetrazol-5-yl)phenyl]-3-pyridinyl]methyl]-2H-imidazol-2-one;

1-(1-isobutyl-1H-imidazol-2-yl)-4-butyl-1,3-dihydro-3-[[4-[4-(1H-tetrazol-5-yl)phenyl]-3-pyridinyl]methyl]-2H-imidazol-2-one and 1-(1-tertbutyl-1H-imidazol-2-yl)-4-butyl-1,3-dihydro-3-[[4-[4-(1H-tetrazol-5-yl)phenyl]-3-pyridinyl]methyl]-2H-imidazol-2-one.

Within this second group of compounds of Formula III there is a fifth class of higher-interest compounds of Formula III(e):

III(e)

wherein R¹ is selected from hydrido, methyl, ethyl, n-propyl, isopropyl, n-butyl, tert-butyl, sec-butyl, isobutyl and n-pentyl; wherein each of R³ and R⁴ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(e) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-ethyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-propyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-isopropyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-butyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-secbutyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-isobutyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-tertbutyl-1H-imidazol-2-yl)-4-propyl-1,3-dihydro-3-[[4-[3-(1H-tetrazol-5-yl)phenyl]-4-pyridinyl]methyl]-2H-imidazol-2-one;

1-(1-methyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-ethyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-propyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-isopropyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-butyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-secbutyl-1H-imidazol-2-yl)-4-butyl-1,3-dihydro-3-[[4-[3-(1H-tetrazol-5-yl)phenyl]-4-pyridinyl]methyl]-2H-imidazol-2-one;

1-(1-isobutyl-1H-imidazol-2-yl)-4-butyl-1,3-dihydro-3-[[4-[3-(1H-tetrazol-5-yl)phenyl]-4-pyridinyl]methyl]-2H-imidazol-2-one and 1-(1-tertbutyl-1H-imidazol-2-yl)-4-butyl-1,3-dihydro-3-[[4-[3-(1H-tetrazol-5-yl)phenyl]-4-pyridinyl]methyl]-2H-imidazol-2-one.

Within this second group of compounds of Formula III there is a sixth class of higher-interest compounds of Formula III(f):

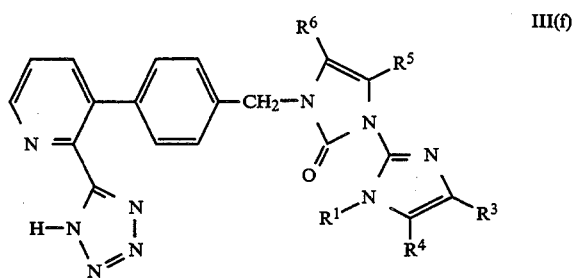

wherein $R^1$ is selected from hydrido, methyl, ethyl, n-propyl, isopropyl, n-butyl, tert-butyl, sec-butyl, isobutyl and n-pentyl; wherein each of $R^3$ and $R^4$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula III(f) consists of compounds and their stereoisomers and tautomers and the pharmaceutically-acceptable salts thereof, said compounds consisting of 1-(1-methyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-ethyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-propyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-isopropyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-butyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-secbutyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-isobutyl-1H-imidazol-2-yl)-4-propyl-1,3-dihydro-3-[[4-[2-(1H-tetrazol-5-yl)phenyl]-3-pyridinyl]methyl]-2H-imidazol-2-one;

1-(1-tertbutyl-1H-imidazol-2-yl)-4-propyl-1,3-dihydro-[2-(1H-tetrazol-5-yl)phenyl]-3-pyridinyl]methyl]-2H-imidazol-2-one;

1-(1-methyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-ethyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-propyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-isopropyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-butyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-secbutyl-1H-imidazol-2-yl)-4-butyl-1,3-dihydro-3-[[4-[2-(1H-tetrazol-5-yl)phenyl]-3-pyridinyl]methyl]-2H-imidazol-2-one;

1-(1-isobutyl-1H-imidazol-2-yl)-4-butyl-1,3-dihydro-3-[[4-[2-(1H-tetrazol-5-yl)phenyl]-3-pyridinyl]methyl]-2H-imidazol-2-one and 1-(1-tertbutyl-1H-imidazol-2-yl)-4-butyl-1,3-dihydro-3-[[4-[2-(1H-tetrazol-5-yl)phenyl]-3-pyridinyl]methyl]-2H-imidazol-2-one.

Within the compounds of Formula I there is a third group of compounds of more interest as represented by Formula IV:

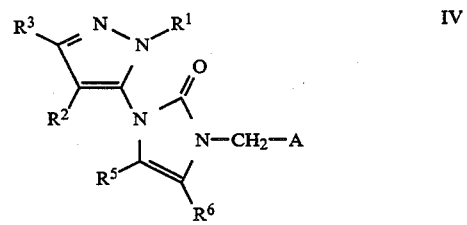

wherein $R^1$ is selected from hydrido and alkyl; wherein each of $R^2$ and $R^3$ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

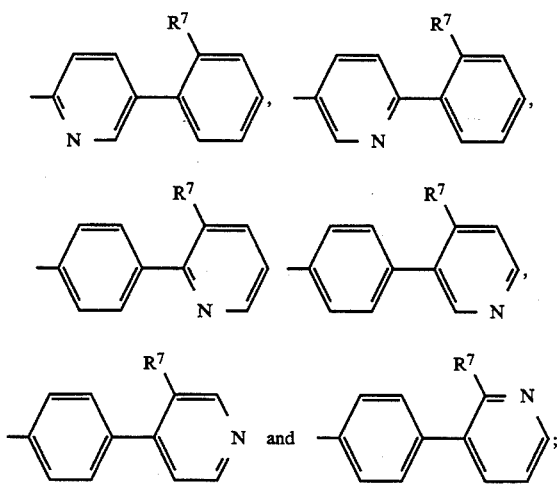

wherein R⁷ is an acidic group selected from COOH and

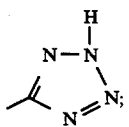

or a stereoisomer or a tautomer thereof or a pharmaceutically-acceptable salt thereof.

Within this third group of compounds of Formula IV there is a first class of higher-interest compounds of Formula IV(a):

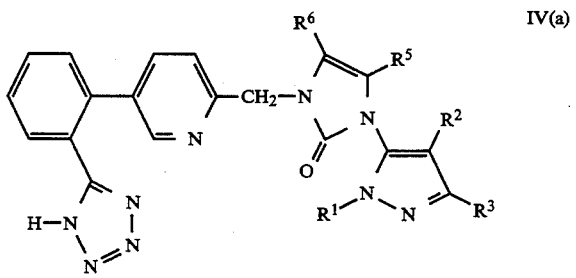

wherein $R^1$ is selected from hydrido, methyl, ethyl, n-propyl, isopropyl, n-butyl, tert-butyl, sec-butyl, isobutyl and n-pentyl; wherein each of $R^2$ and $R^3$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(a) consists of compounds and their stereoisomers and tautomers and the pharmaceutically-acceptable salts thereof, said compounds consisting of 1-(1-methyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-ethyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-propyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-butyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-secbutyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isobutyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-tertbutyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1,4-dimethyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-ethyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-isopropyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-carbomethoxy-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-carboxy-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-acetyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-methyl-4-chloro-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-methyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-ethyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1,4-diisopropyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-carbomethoxy-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-carboxy-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-acetyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-4-chloro-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1-ethyl-4-methyl-1H-pyrazol-5-yl)-4-butyl-1,3-dihydro-3-[[5-[2-(1H-tetrazol-5-yl)phenyl]-2-pyridinyl]methyl]-2H-imidazol-2-one;

1-(1,4-diethyl-1H-pyrazol-5-yl)-4-butyl-1,3-dihydro-
3-[[5-[2-(1H-tetrazol-5-yl)phenyl]-2-pyridinyl]me-
thyl]-2H-imidazol-2-one;

1-(1-ethyl-4-isopropyl-1H-pyrazol-5-yl)-4-butyl-1,3-
dihydro-3-[[5-[2-(1H-tetrazol-5-yl)phenyl]-2-
pyridinyl]methyl]-2H-imidazol-2-one;

1-(1-ethyl-4-carbomethoxy-1H-pyrazol-5-yl)-4-butyl-
1,3-dihydro-3-[[5-[2-(1H-tetrazol-5-yl)phenyl]-2-
pyridinyl]methyl]-2H-imidazol-2-one;

1-(1-ethyl-4-carboxy-1H-pyrazol-5-yl)-4-butyl-1,3-
dihydro-3-[[5-[2-(1H-tetrazol-5-yl)phenyl]-2-
pyridinyl]methyl]-2H-imidazol-2-one;

1-(1-ethyl-4-acetyl-1H-pyrazol-5-yl)-4-butyl-1,3-
dihydro-3-[[5-[2-(1H-tetrazol-5-yl)phenyl]-2-
pyridinyl]methyl]-2H-imidazol-2-one and 1-(1-ethyl-4-chloro-1H-pyrazol-5-yl)-4-butyl-1,3-
dihydro-3-[[5-[2-(1H-tetrazol-5-yl)phenyl]-2-
pyridinyl]methyl]-2H-imidazol-2-one.

Within this third group of compounds of Formula IV there is a second class of higher-interest compounds of Formula IV(b):

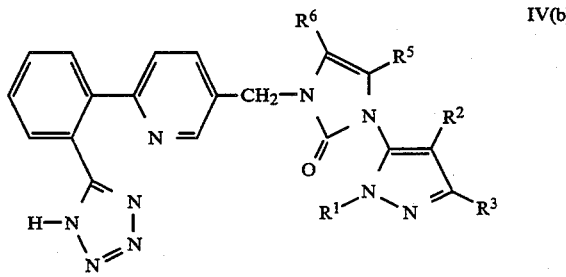

wherein $R^1$ is selected from hydrido, methyl, ethyl, n-propyl, isopropyl, n-butyl, tert-butyl, sec-butyl, isobutyl and n-pentyl; wherein each of $R^2$ and $R^3$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(b) consists of compounds and their stereoisomers and tautomers and the pharmaceutically-acceptable salts thereof, said compounds consisting of 1-(1-methyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-propyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-butyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-secbutyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isobutyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-tertbutyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1,4-dimethyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-ethyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-isopropyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-carbomethoxy-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-carboxy-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-acetyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-methyl-4-chloro-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-4-methyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-4-ethyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1,4-diisopropyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-4-carbomethoxy-1H-pyrazol-5-yl)-4-butyl-1,3-dihydro-3-[[6-[2-(1H-tetrazol-5-yl)phenyl]-3-pyridinyl]methyl]-2 H-imidazol-2-one;

1-(1-isopropyl-4-carboxy-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-4-acetyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-4-chloro-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-4-methyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1,4-diethyl-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-4-isopropyl-1H-pyrazol-5-yl)-4-butyl-1,3-dihydro3-[[6-[2-(1H-tetrazol-5-yl)phenyl]-3-pyridinyl]methyl]-2H-imidazol-2-one;

1-(1-ethyl-4-carbomethoxy-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-4-carboxy-1H-pyrazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-4-acetyl-1H-pyrazol-5-yl)-4-butyl-1,3-dihydro-3-[[6-[2-(1H-tetrazol-5-yl)phenyl]-3-pyridinyl]methyl]-2H-imidazol-2-one and 1-(1-ethyl-4-chloro-1H-pyrazol-5-yl)-4-butyl-1,3-dihydro-3-[[6-[2-(1H-tetrazol-5-yl)phenyl]-3-pyridinyl]methyl]-2H-imidazol-2-one.

Within this third group of compounds of Formula IV there is a third class of higher-interest compounds of Formula IV(c):

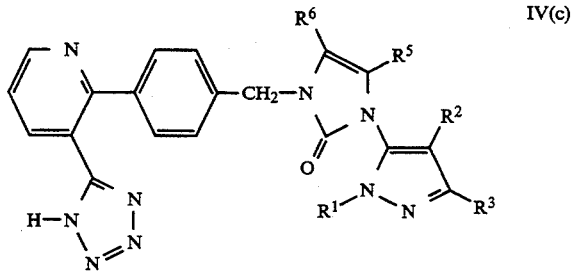

wherein $R^1$ is selected from hydrido, methyl, ethyl, n-propyl, isopropyl, n-butyl, tert-butyl, sec-butyl, isobutyl and n-pentyl; wherein each of $R^2$ and $R^3$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(c) consists of compounds and their stereoisomers and tautomers and the pharmaceutically-acceptable salts thereof, said compounds consisting of 1-(1-methyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-propyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-butyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-secbutyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isobutyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-tertbutyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1,4-dimethyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-ethyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-isopropyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-carbomethoxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-carboxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-acetyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-methyl-4-chloro-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-methyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-ethyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1,4-diisopropyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-carbomethoxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-carboxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-acetyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-4-chloro-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-4-methyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1,4-diethyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-4-isopropyl-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-4-carbomethoxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-4-carboxy-1H-pyrazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-4-acetyl-1H-pyrazol-5-yl)-4-butyl-1,3-dihydro-3-[[4-[3-(1H-tetrazol-5-yl)phenyl]-2-pyridinyl]methyl]-2H-imidazol-2-one and 1-(1-ethyl-4-chloro-1H-pyrazol-5-yl)-4-butyl-1,3-dihydro-3-[[4-[3-(1H-tetrazol-5-yl)phenyl]-2-pyridinyl]methyl]-2H-imidazol-2-one.

Within this third group of compounds of Formula IV there is a fourth class of higher-interest compounds of Formula IV(d):

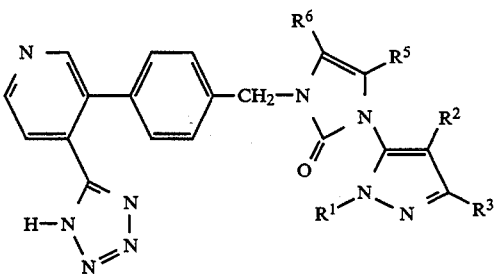

IV(d)

wherein R¹ is selected from hydrido, methyl, ethyl, n-propyl, isopropyl, n-butyl, tert-butyl, sec-butyl, isobutyl and n-pentyl; wherein each of R² and R³ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(d) consists of compounds and their stereoisomers and tautomers and the pharmaceutically-acceptable salts thereof, said compounds consisting of 1-(1-methyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-ethyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-propyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-butyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-secbutyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isobutyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-tertbutyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1,4-dimethyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-ethyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-isopropyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-carbomethoxy-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-carboxy-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-acetyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-methyl-4-chloro-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-methyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-ethyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1,4-diisopropyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-carbomethoxy-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-carboxy-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-acetyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-isopropyl-4-chloro-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-ethyl-4-methyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1,4-diethyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-ethyl-4-isopropyl-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-ethyl-4-carbomethoxy-1H-pyrazol-5-yl)-4-butyl-1,3-dihydro-3-[[4-[4-(1H-tetrazol-5-yl)phenyl]-3-pyridinyl]methyl]-2 H-imidazol-2-one;
1-(1-ethyl-4-carboxy-1H-pyrazol-5-yl)-4-butyl-1,3-dihydro-3-[[4-[4-(1H-tetrazol-5-yl)phenyl]-3-pyridinyl]methyl]-2H-imidazol-2-one;
1-(1-ethyl-4-acetyl-1H-pyrazol-5-yl)-4-butyl-1,3-dihydro-3-[[4-[4-(1H-tetrazol-5-yl)phenyl]-3-pyridinyl]methyl]-2H-imidazol-2-one and
1-(1-ethyl-4-chloro-1H-pyrazol-5-yl)-4-butyl-1,3-dihydro-3-[[4-[4-(1H-tetrazol-5-yl)phenyl]-3-pyridinyl]methyl]-2H-imidazol-2-one.

Within this third group of compounds of Formula IV there is a fifth class of higher-interest compounds of Formula IV(e):

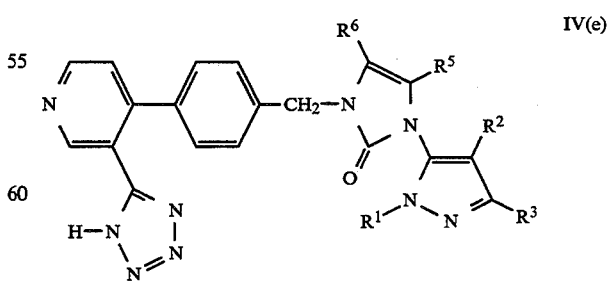

IV(e)

wherein R¹ is selected from hydrido, methyl, ethyl, n-propyl, isopropyl, n-butyl, tert-butyl, sec-butyl, isobutyl and n-pentyl; wherein each of R² and R³ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(e) consists of compounds and their stereoisomers and tautomers and the pharmaceutically-acceptable salts thereof, said compounds consisting of 1-(1-methyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-propyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-butyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-secbutyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isobutyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-tertbutyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1,4-dimethyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-methyl-4-ethyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-methyl-4-isopropyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-methyl-4-carbomethoxy-1H-pyrazol-5-yl)-4-butyl-1,3-dihydro-3-[[4-[3-(1H-tetrazol-5-yl)phenyl]-4-pyridinyl]methyl]-2 H-imidazol-2-one;

1-(1-methyl-4-carboxy-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-methyl-4-acetyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-methyl-4-chloro-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-methyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-ethyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1,4-diisopropyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-carbomethoxy-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-carboxy-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-acetyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-4-chloro-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-4-methyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1,4-diethyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-4-isopropyl-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-4-carbomethoxy-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-4-carboxy-1H-pyrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-4-acetyl-1H-pyrazol-5-yl)-4-butyl-1,3-dihydro-3-[[4-[3-(1H-tetrazol-5-yl)phenyl]-4-pyridinyl]methyl]-2H-imidazol-2-one and 1-(1-ethyl-4-chloro-1H-pyrazol-5-yl)-4-butyl-1,3-dihydro-3-[[4-[3-(1H-tetrazol-5-yl)phenyl]-4-pyridinyl]methyl]-2H-imidazol-2-one.

Within this third group of compounds of Formula IV there is a sixth class of higher-interest compounds of Formula IV(f):

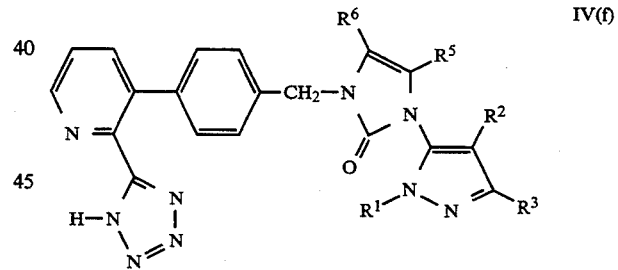

IV(f)

wherein $R^1$ is selected from hydrido, methyl, ethyl, n-propyl, isopropyl, n-butyl, tert-butyl, sec-butyl, isobutyl and n-pentyl; wherein each of $R^2$ and $R^3$ may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula IV(f) consists of compounds and their stereoisomers and tautomers and the pharmaceutically-acceptable salts thereof, said compounds consisting of 1-(1-methyl-1H-pyrazol-5-yl)-4-butyl-1, 3-dihydro-3-[[4-[2-(1H-tetrazol-5-yl)phenyl]-3-pyridinyl]methyl]-2H-imidazol-2-one;

1-(1-ethyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-propyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-butyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-secbutyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isobutyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-tertbutyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1,4-dimethyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-ethyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-isopropyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-carbomethoxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-carboxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-acetyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-methyl-4-chloro-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-methyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-ethyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1,4-diisopropyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-carbomethoxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-carboxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-acetyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-4-chloro-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-4-methyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1,4-diethyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-4-isopropyl-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-4-carbomethoxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-4-carboxy-1H-pyrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-4-acetyl-1H-pyrazol-5-yl)-4-butyl-1,3-dihydro-3-[[4-[2-(1H-tetrazol-5-yl)phenyl]-3-pyridinyl]methyl]-2H-imidazol-2-one and 1-(1-ethyl-4-chloro-1H-pyrazol-5-yl)-4-butyl-1,3-dihydro-3-[[4-[2-(1H-tetrazol-5-yl)phenyl]-3-pyridinyl]methyl]-2H-imidazol-2-one.

Within the compounds of Formula I there is a fourth group of compounds of more interest as represented by Formula V:

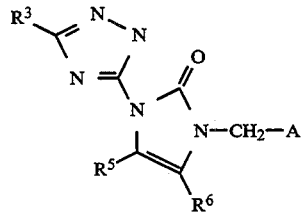

wherein $R^1$ is selected from hydrido and alkyl; wherein $R^3$ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

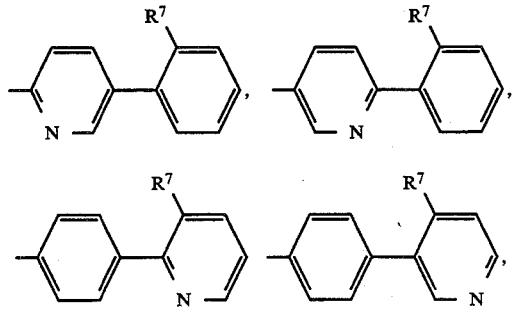

-continued

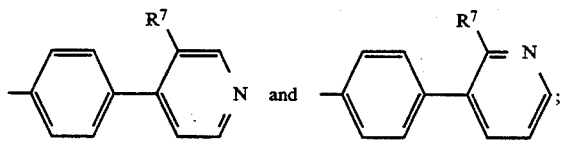

wherein R⁷ is an acidic group selected from COOH and

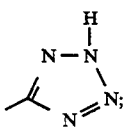

or a stereoisomer or a tautomer thereof or a pharmaceutically-acceptable salt thereof.

Within this fourth group of compounds of Formula V there is a first class of higher-interest compounds of Formula V(a):

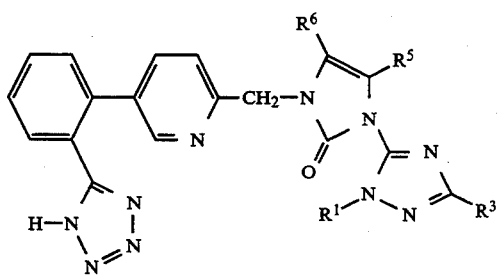

wherein R¹ is selected from hydrido, methyl, ethyl, n-propyl, isopropyl, n-butyl, tert-butyl, sec-butyl, isobutyl and n-pentyl; wherein R² may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(a) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[5-[2-(1H-tetrazol-5-yl)phenyl]-2-pyridinyl]-methyl]-2H-imidazol-2-one;

1-(1-ethyl-N-1,2,4-triazol-5-yl)-4-propyl-1,3-dihydro-3-[[5-[2-(1H-tetrazol-5-yl)phenyl]-2-pyridinyl]methyl]-2H-imidazol-2-one;

1-(1-propyl-1H-1,2,4-triazol-5-yl)-4-propyl-1,3-dihydro-3-[[5-[2-(1H-tetrazol-5-yl)phenyl]-2-pyridinyl]methyl]-2H-imidazol-2-one;

1-(1-isopropyl-1H-1, 2,4-triazol-5-yl)-4-propyl-1,3-dihydro-3-[[5-[2-(1H-tetrazol-5-yl)phenyl]-2-pyridinyl]methyl]-2H-imidazol-2-one;

1-(1-butyl-1H-1,2,4-triazol-5-yl)-4-propyl-1,3-dihydro-3-[[5-[2-(1H-tetrazol-5-yl)phenyl]-2-pyridinyl]methyl]-2H-imidazol-2-one;

1-(1-secbutyl-1H-1,2,4-triazol-5-yl)-4-propyl-1,3-dihydro-3-[[5-[2-(1H-tetrazol-5-yl)phenyl]-2-pyridinyl]methyl]-2H-imidazol-2-one;

1-(1-isobutyl-1H-1,2,4-triazol-5-yl)-4-propyl-1,3-dihydro-3-[[5-[2-(1H-tetrazol-5-yl)phenyl]-2-pyridinyl]-2H-imidazol-2-one;

1-(1-tertbutyl-1H-1,2,4-triazol-5-yl)-4-propyl-1,3-dihydro-3-[[5-[2-(1H-tetrazol-5-yl)phenyl]-2-pyridinyl]-2H-imidazol-2-one;

1-(1-methyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-ethyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-propyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-butyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-secbutyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one;

1-(1-isobutyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one and 1-(1-tertbutyl-1H-1,2,4-triazol-5-yl)-4-butyl-1,3-dihydro-3-[[5-[2-(1H-tetrazol-5-yl)phenyl]-2-pyridinyl]methyl]-2H-imidazol-2-one.

Within this fourth group of compounds of Formula V there is a second class of higher-interest compounds of Formula V(b):

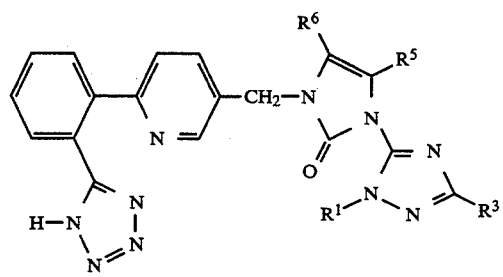

wherein R¹ is selected from hydrido, methyl, ethyl, n-propyl, isopropyl, n-butyl, tert-butyl, sec-butyl, isobutyl and n-pentyl; wherein R³ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(b) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[6-[2-(1H-tetrazol-5-yl)phenyl]-3-pyridinyl]-methyl]-2H-imidazol-2-one;

1-(1-ethyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-propyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-isopropyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-butyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-secbutyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-isobutyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-tertbutyl-1H-1,2,4-triazol-5-yl)-4-propyl-1,3-dihydro-3-[[6-[2-(1H-tetrazol-5-yl)phenyl]-3-pyridinyl]methyl]-2H-imidazol-2-one;

1-(1-methyl-ill-i, 2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-ethyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-propyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-isopropyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-butyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-secbutyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one;

1-(1-isobutyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one and 1-(1-tertbutyl-1H-1,2,4-triazol-5-yl)-4-butyl-1,3-dihydro-3-[[6-[2-(1H-tetrazol-5-yl)phenyl]-3-pyridinyl]methyl]-2H-imidazol-2-one.

Within this fourth group of compounds of Formula V there is a third class of higher-interest compounds of Formula V(c):

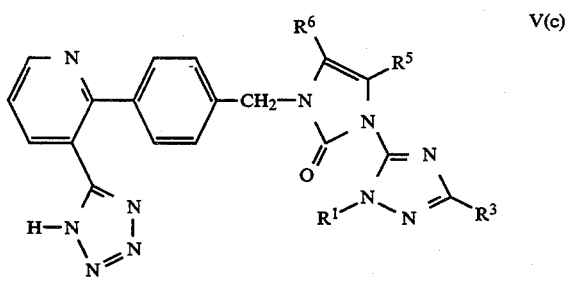

wherein $R^1$ is selected from hydrido, methyl, ethyl, n-propyl, isopropyl, n-butyl, tert-butyl, sec-butyl, isobutyl and n-pentyl; wherein $R^3$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(c) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-ethyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-propyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-isopropyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-butyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-secbutyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-isobutyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-tertbutyl-1H-1,2,4-triazol-5-yl)-4-propyl-1,3-dihydro-3-[[4-[3-(1H-tetrazol-5-yl)phenyl]-2-pyridinyl]methyl]-2H-imidazol-2-one;

1-(1-methyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-ethyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-propyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-isopropyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-butyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-secbutyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one;

1-(1-isobutyl-1H-1,2,4-triazol-5-yl)-4-butyl-1,3-dihydro-3-[[4-[3-(1H-tetrazol-5-yl)phenyl]-2-pyridinyl]methyl]-2H-imidazol-2-one and 1-(1-tertbutyl-1H-1, 2,4-triazol-5-yl)-4-butyl-1,3-dihydro-3-[[4-[3-(1H-tetrazol-5-yl)phenyl]-2-pyridinyl]methyl]-2H-imidazol-2-one.

Within this fourth group of compounds of Formula V there is a fourth class of higher-interest compounds of Formula V(d):

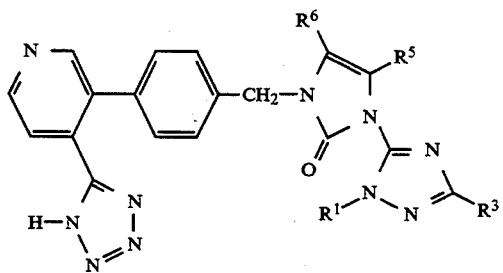

V(d)

wherein R¹ is selected from hydrido, methyl, ethyl, n-propyl, isopropyl, n-butyl, tert-butyl, sec-butyl, isobutyl and n-pentyl; wherein R³ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(d) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-ethyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-propyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-isopropyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-butyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-secbutyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-isobutyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-tertbutyl-1H-1,2,4-triazol-5-yl)-4-propyl-1,3-dihydro-3-[[4-[4-(1H-tetrazol-5-yl)phenyl]-3-pyridinyl]methyl]-2H-imidazol-2-one;

1-(1-methyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-ethyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-propyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-isopropyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-butyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-secbutyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one;

1-(1-isobutyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one and 1-(1-tertbutyl-1H-1,2,4-triazol-5-yl)-4-butyl-1,3-dihydro-3-[[4-[4-(1H-tetrazol-5-yl)phenyl]-3-pyridinyl]methyl]-2H-imidazol-2-one.

Within this fourth group of compounds of Formula V there is a fifth class of higher-interest compounds of Formula V(e):

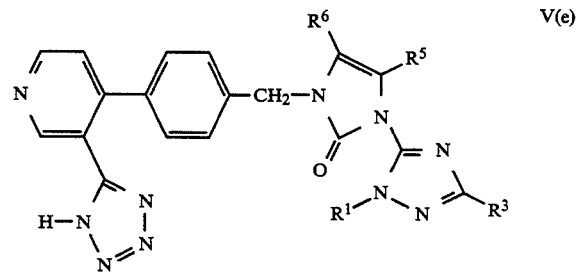

V(e)

wherein R¹ is selected from hydrido, methyl, ethyl, n-propyl, isopropyl, n-butyl, tert-butyl, sec-butyl, isobutyl and n-pentyl; wherein R³ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(e) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-ethyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-propyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-isopropyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-butyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-secbutyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-isobutyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-tertbutyl-1H-1,2,4-triazol-5-yl)-4-propyl-1,3-dihydro-3-[[4-[3-(1H-tetrazol-5-yl)phenyl]-4-pyridinyl]methyl]-2H-imidazol-2-one;

1-(1-methyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-propyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-butyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-secbutyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one;

1-(1-isobutyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one and 1-(1-tertbutyl-1H-1,2,4-triazol-5-yl)-4-butyl-1,3-dihydro-3-[[4-[3-(1H-tetrazol-5-yl)phenyl]-4-pyridinyl]methyl]-2H-imidazol-2-one.

Within this fourth group of compounds of Formula V there is a sixth class of higher-interest compounds of Formula V(f):

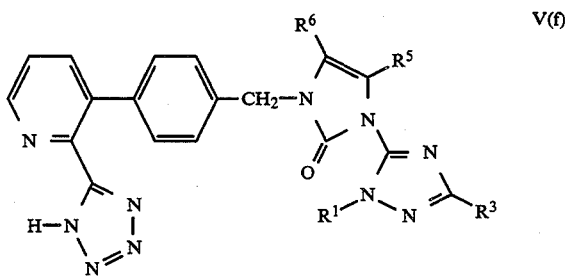

wherein $R^1$ is selected from hydrido, methyl, ethyl, n-propyl, isopropyl, n-butyl, tert-butyl, sec-butyl, isobutyl and n-pentyl; wherein $R^3$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula V(f) consists of compounds and their stereoisomers and tautomers and the pharmaceutically-acceptable salts thereof, said compounds consisting of 1-(1-methyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-ethyl-IN-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-propyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-isopropyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-butyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-secbutyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-isobutyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-tertbutyl-1H-1,2,4-triazol-5-yl)-4-propyl-1,3-dihydro-3-[[4-[2-(1H-tetrazol-5-yl)phenyl]-3-pyridinyl]methyl]-2H-imidazol-2-one;

1-(1-methyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-propyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-isopropyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-butyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-secbutyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one;

1-(1-isobutyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one and 1-(1-tertbutyl-1H-1,2,4-triazol-5-yl)-4-butyl-1,3-dihydro-3-[[4-[2-(1H-tetrazol-5-yl)phenyl]-3-pyridinyl]methyl]-2H-imidazol-2-one.

Within the compounds of Formula I there is a fifth group of compounds of more interest as represented by Formula VI:

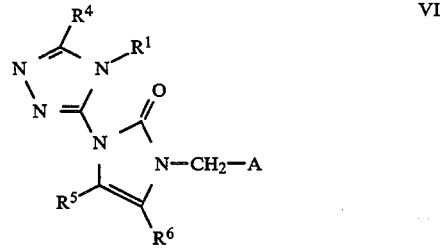

wherein $R^1$ is selected from hydrido and alkyl; wherein $R^4$ is selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

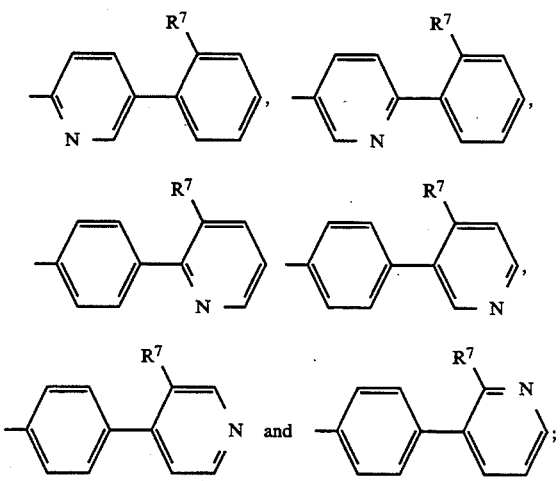

wherein R⁷ is an acidic group selected from COOH and

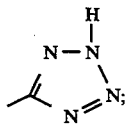

or a stereoisomer or a tautomer thereof or a pharmaceutically-acceptable salt thereof.

Within this fifth group of compounds of Formula VI there is a first class of higher-interest compounds of Formula VI(a):

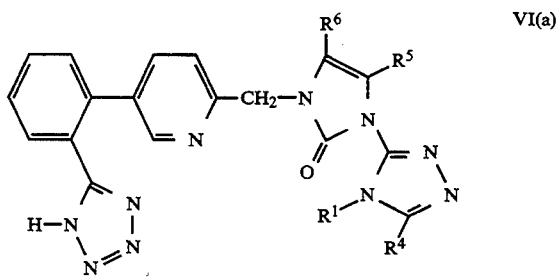

VI(a)

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI (a) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-ethyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-propyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-isopropyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-butyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-secbutyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-isobutyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-tertbutyl-4H-1,2,4-triazol-3-yl)-4-propyl-1,3-dihydro-3-[[5-[2-(1H-tetrazol-5-yl)phenyl]-2-pyridinyl]methyl]-2H-imidazol-2-one;

1-(4-methyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-ethyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-propyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-isopropyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-butyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-secbutyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one;

1-(4-isobutyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one and 1-(4-tertbutyl-4H-1,2,4-triazol-3-yl)-4-butyl-1,3-dihydro-3-[[5-[2-(1H-tetrazol-5-yl)phenyl]-2-pyridinyl]methyl]-2H-imidazol-2-one.

Within this fifth group of compounds of Formula VI there is a second class of higher-interest compounds of Formula VI(b):

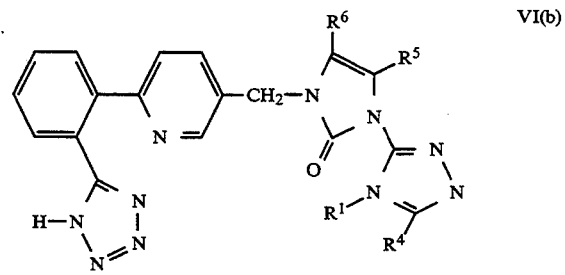

VI(b)

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, secbutyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI (b) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-ethyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-propyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-isopropyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-butyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-secbutyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-isobutyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-tertbutyl-4H-1,2,4-triazol-3-yl)-4-propyl-1,3-dihydro-3-[[6-[2-(1H-tetrazol-5-yl)phenyl]-3-pyridinyl]methyl]-2H-imidazol-2-one;

1-(4-methyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-ethyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-propyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-isopropyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-butyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-secbutyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one;

1-(4-isobutyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one and 1-(4-tertbutyl-4H-1,2,4-triazol-3-yl)-4-butyl-1,3-dihydro-3-[[6-[2-(1H-tetrazol-5-yl)phenyl]-3-pyridinyl]methyl]-2H-imidazol-2-one.

Within this fifth group of compounds of Formula VI there is a third class of higher-interest compounds of Formula VI(c):

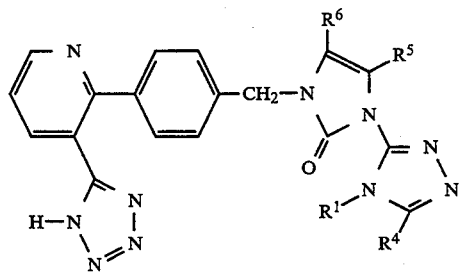

VI(c)

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI(c) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-ethyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-propyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-isopropyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-butyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-secbutyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-isobutyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-tertbutyl-4H-1,2,4-triazol-3-yl)-4-propyl-1,3-dihydro-3-[[4-[3-(1H-tetrazol-5-yl)phenyl]-2-pyridinyl]methyl]-2H-imidazol-2-one;

1-(4-methyl-4H-1,2,4-triazol-3-yl)-4-butyl-1,3-dihydro-3-[[4-[3-(1H-tetrazol-5-yl)phenyl]-2-pyridinyl]methyl]-2H-imidazol-2-one;

1-(4-ethyl-4H-1,2,4-triazol-3-yl)-4-butyl-1,3-dihydro-3-[[4-[3-(1H-tetrazol-5-yl)phenyl]-2-pyridinyl]methyl]-2H-imidazol-2-one;

1-(4-propyl-4H-1,2,4-triazol-3-yl)-4-butyl-1,3-dihydro-3-[[4-[3-(1H-tetrazol-5-yl)phenyl]-2-pyridinyl]methyl]-2H-imidazol-2-one;

1-(4-isopropyl-4H-1,2,4-triazol-3-yl)-4-butyl-1,3-dihydro-3-[[3-(1H-tetrazol-5 -yl)phenyl]-2-pyridinyl]methyl]-2H-imidazol-2-one;

-(4-butyl-4H-1,2,4-triazol-3-yl)-4-butyl-1,3-dihydro-3-[[4-[3-(1H-tetrazol-5-yl)phenyl]-2-pyridinyl]methyl]-2H-imidazol-2-one;

1-(4-secbutyl-4H-1,2,4-triazol-3-yl)-4-butyl-1,3-dihydro-3-[[4-[3-(1H-tetrazol-5-yl)phenyl]-2-pyridinyl]methyl]-2H-imidazol-2-one;

1-(4-isobutyl-4H-1,2,4-triazol-3 -yl)-4-butyl-1,3-dihydro-3-[[4-[3-(1H-tetrazol-5-yl)phenyl]-2-pyridinyl]methyl]-2H-imidazol-2-one and 1-(4-tertbutyl-4H-1,2,4-triazol-3-yl)-4-butyl-1,3-dihydro-3-[[4-[3-(1H-tetrazol-5-yl)phenyl]-2 -pyridinyl]methyl]-2H-imidazol-2 -one.

Within this fifth group of compounds of Formula VI there is a fourth class of higher-interest compounds of Formula VI(d):

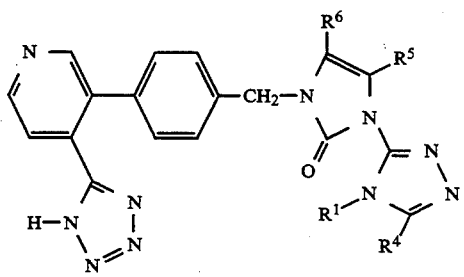

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI(d) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-ethyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-propyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-isopropyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-butyl-4H-1,2,4-triazol-3-yl)-4-propyl-1,3-dihydro-3-[[4-[4-(1H-tetrazol-5-yl)phenyl]-3 -pyridinyl]methyl]-2H-imidazol-2-one;

1-(4-secbutyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-isobutyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-tertbutyl-4H-1,2,4-triazol-3-yl)-4-propyl-1,3-dihydro-3-[[4-[4-(1H-tetrazol-5-yl)phenyl]-3-pyridinyl]methyl]-2H-imidazol-2-one;

1-(4-methyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one;

1-(4-ethyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one;

1-(4-propyl-4H-1,2,4-triazol-3-yl) -4-butyl-1,3-dihydro-3-[[4-[4- (1H-tetrazol-5-yl)phenyl]-3-pyridinyl]methyl]-2H-imidazol-2-one;

-(4-isopropyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one;

1-(4-butyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one;

1-(4-secbutyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one;

1-(4-isobutyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2-one and 1-(4-tertbutyl-4H-1,2,4-triazol-3-yl)-4-butyl-1,3-dihydro-3-[[4-[4-(1H-tetrazol-5-yl)phenyl]-3-pyridinyl]methyl]-2H-imidazol-2 -one.

Within this fifth group of compounds of Formula VI where is a fifth class of higher-interest compounds of Formula VI(e):

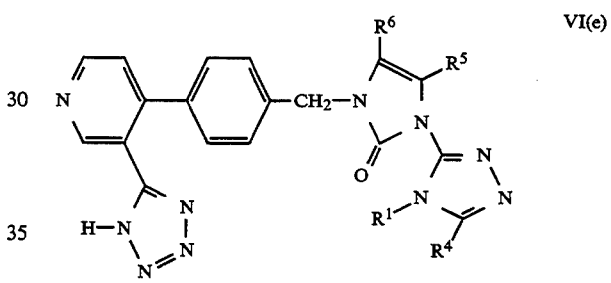

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI (e) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-ethyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-propyl-4H-1,2,4-triazol-3-yl)- 4-propyl-1,3-dihydro-3-[[4-[3-(1H-tetrazol-5-yl)phenyl]-4-pyridinyl]methyl]-2H-imidazol-2-one;

1-(4-isopropyl-4H-1,2,4-triazol-3-yl)-4-propyl-1,3-dihydro-3-[[4-[3-(1H-tetrazol-5 -yl)phenyl]-4-pyridinyl]methyl]-2H-imidazol-2-one;

1-(4-butyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-secbutyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-isobutyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-tertbutyl-4H-1,2,4-triazol-3-yl)-4-propyl-1,3-dihydro-3-[[4-[3-(1H-tetrazol-5-yl)phenyl]-4-pyridinyl]methyl]-2H-imidazol-2-one;

1-(4-methyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-ethyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-propyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-isopropyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-butyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-secbutyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one;

1-(4-isobutyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one and 1-(4-tertbutyl-4H-1,2,4-triazol-3-yl)-4-butyl-1,3-dihydro-3-[[4-[3-(1H-tetrazol-5-yl)phenyl]-4-pyridinyl]methyl]-2H-imidazol-2-one.

Within this fifth group of compounds of Formula VI there is a sixth class of higher-interest compounds of Formula VI(f):

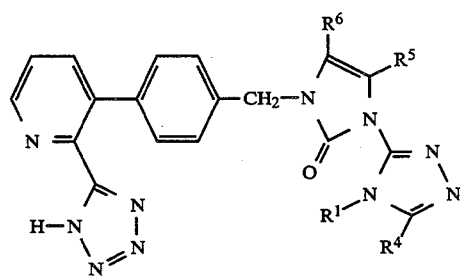

wherein $R^1$ is selected from hydrido, methyl, ethyl, n-propyl, isopropyl, n-butyl, tert-butyl, sec-butyl, isobutyl and n-pentyl; wherein $R^4$ may be selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VI(f) consists of compounds and their stereoisomers and tautomers and the pharmaceutically-acceptable salts thereof, said compounds consisting of 1-(4-methyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-ethyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-propyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-isopropyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-butyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-secbutyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-isobutyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-tertbutyl-4H-1,2,4-triazol-3-yl)-4-propyl-1,3-dihydro-3-[[4-[2-(1H-tetrazol-5-yl)phenyl]-3-pyridinyl]methyl]-2H-imidazol-2-one;

1-(4-methyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-( 4-ethyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-(4-propyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-(4-isopropyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-(4-butyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-(4-secbutyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one;

1-(4-isobutyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one and 1-(4-tertbutyl-4H-1,2,4-triazol-3-yl)-4-butyl-1,3-dihydro-3-[[4-[2-(1H-tetrazol-5-yl)phenyl]-3-pyridinyl]methyl]-2H-imidazol-2-one.

Within the compounds of Formula I there is a sixth group of compounds of more interest as represented by Formula VII:

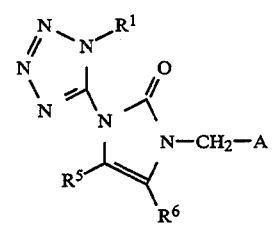

wherein $R^1$ is selected from hydrido and alkyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

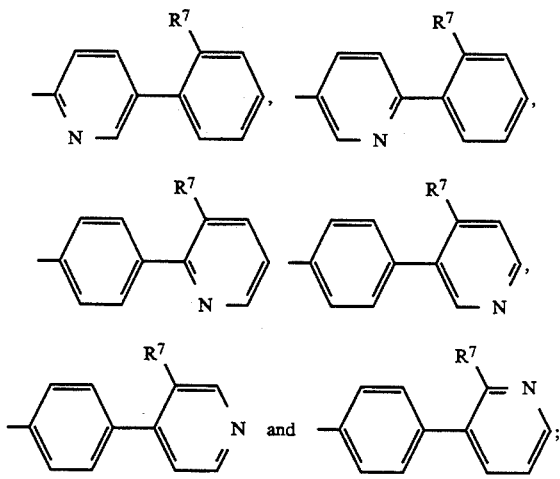

wherein R⁷ is an acidic group selected from COOH and

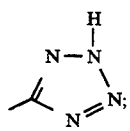

or a stereoisomer or a tautomer thereof or a pharmaceutically-acceptable salt thereof.

Within this second group of compounds of Formula VII there is a first class of higher-interest compounds of Formula VII(a):

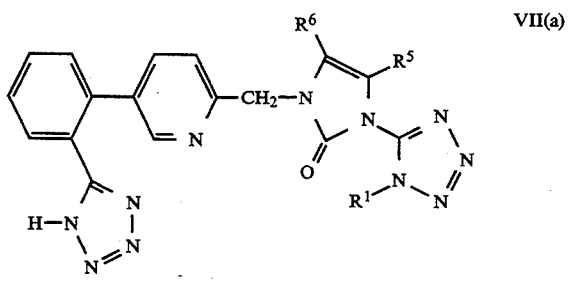

wherein R¹ is selected from hydrido, methyl, ethyl, n-propyl, isopropyl, n-butyl, tert-butyl, sec-butyl, isobutyl and n-pentyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII(a) consists of compounds and their stereoisomers and tautomers and the pharmaceutically-acceptable salts thereof, said compounds consisting of 1-(1-methyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-ethyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-propyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-isopropyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-butyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-secbutyl-1H-tetrazol-5-yl)-4-propyl-1,3-dihydro-3-[[5-[2 -(1H-tetrazol-5-yl)phenyl]-2-pyridinyl]methyl]-2H-imidazol-2-one;

1-(1-isobutyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-tertbutyl-1H-tetrazol-5-yl)-4-propyl-1,3-dihydro-3-[[5-[2-(1H-tetrazol-5-yl)phenyl]-2-pyridinyl]methyl]-2H-imidazol-2-one;

1-(1-methyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-ethyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-propyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-isopropyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-butyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-secbutyl-1H-tetrazol-5-yl)-4-butyl-1,3-dihydro-3-[[5-[2-(1H-tetrazol-5-yl)phenyl]-2-pyridinyl]methyl]-2H-imidazol-2-one;

1-(1-isobutyl-1H-tetrazol-5-yl)-4-butyl-1,3-dihydro-3-[[5-[2-(1H-tetrazol-5-yl)phenyl]- 2-pyridinyl]methyl]-2H-imidazol-2-one and 1-(1-tertbutyl-1H-tetrazol-5-yl)-4-butyl-1,3-dihydro-3-[[5-[2-(1H-tetrazol-5-yl)phenyl]-2-pyridinyl]methyl]-2H-imidazol-2 -one.

Within this second group of compounds of Formula VII there is a second class of higher-interest compounds of Formula VII(b):

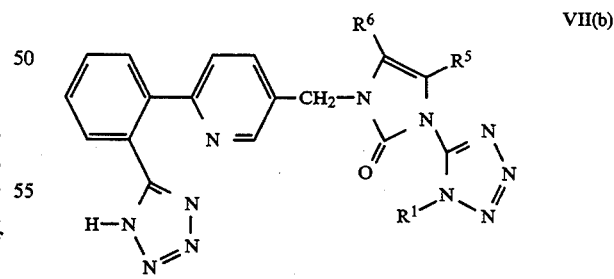

wherein R¹ is selected from hydrido, methyl, ethyl, n-propyl, isopropyl, n-butyl, tert-butyl, sec-butyl, isobutyl and n-pentyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII(b) consists of compounds and their stereoisomers and tautomers and the pharmaceutically-acceptable salts thereof, said compounds consisting of
1-(1-methyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-ethyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-propyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-isopropyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-butyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-secbutyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-isobutyl-1H-tetrazol-5-yl)-4-propyl-1,3-dihydro-3-[[6-2-(1H-tetrazol-5-yl)phenyl]-3-pyridinyl]methyl]-2H-imidazol-2-one;
1-(1-tertbutyl-1H-tetrazol-5-yl)-4-propyl-1,3-dihydro-3-[[6-[2-(1H-tetrazol-5-yl)phenyl]-3-pyridinyl]methyl]-2H-imidazol-2-one;
1-(1-methyl-1H-tetrazol-5-yl)-4-butyl-1,3-dihydro-3-[[6-[2-(1H-tetrazol-5-yl)phenyl]-3-pyridinyl]methyl]-2H-imidazol-2-one;
1-(1-ethyl-1H-tetrazol-5-yl)-4-butyl-1,3-dihydro-3-[[6-[2-(1H-tetrazol-5-yl)phenyl]-3-pyridinyl]methyl]-2H-imidazol-2-one;
1-(1-propyl-1H-tetrazol-5-yl)-4-butyl-1,3-dihydro-3-[[6-[2-(1H-tetrazol-5 -yl)phenyl]-3 -pyridinyl]methyl]-2H-imidazol-2 -one;
1-(1-isopropyl-1H-tetrazol-5-yl)-4-butyl-1,3-dihydro-3-[[6-[2-(1H-tetrazol-5-yl)phenyl]-3-pyridinyl]methyl]-2H-imidazol-2- one;
1-(1-butyl-1H-tetrazol-5-yl)-4-butyl-1,3-dihydro-3-[[6-[2-(1H-tetrazol-5-yl)phenyl]-3-pyridinyl]methyl]-2H-imidazol-2-one;
1-(1-secbutyl-1H-tetrazol-5-yl)-4-butyl-1,3-dihydro-3-[[6-[2-(1H-tetrazol-5-yl)phenyl]-3-pyridinyl]methyl]-2H-imidazol-2- one;
1-(1-isobutyl-1H-tetrazol-5-yl)-4-butyl-1,3-dihydro-3-[[6-2-(1H-tetrazol-5-yl)phenyl]-3-pyridinyl]methyl]-2H-imidazol-2-one and
1-(1-tertbutyl-1H-tetrazol-5-yl)-4-butyl-1,3-dihydro-3-[[6-[2-(1H-tetrazol-5-yl)phenyl]-3-pyridinyl]methyl]-2H-imidazol-2-one.

Within this second group of compounds of Formula VII there is a third class of higher-interest compounds of Formula VII(c):

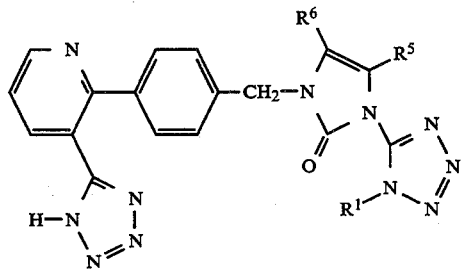

VII(c)

wherein $R^1$ is selected from hydrido, methyl, ethyl, n-propyl, isopropyl, n-butyl, tert-butyl, sec-butyl, isobutyl and n-pentyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII(c) consists of compounds and their stereoisomers and tautomers and the pharmaceutically-acceptable salts thereof, said compounds consisting of
1-(1-methyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-(1-ethyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-(1-propyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-(1-isopropyl-1H-tetrazol-5-yl)-4-propyl-1,3-dihydro-3-[[4-3-(1H-tetrazol-5-yl)phenyl]-2-pyridinyl]methyl]-2H-imidazol-2-one;
1-[1-butyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-[1-secbutyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-(1-isobutyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1-(1-tertbutyl-1H-tetrazol-5-yl)-4-propyl-1,3-dihydro-3-[[4-[3-(1H-tetrazol-5-yl)phenyl]-2-pyridinyl]methyl]-2H-imidazol-2-one;
1(1-methyl-1H-tetrazol-5-yl)-4-butyl-1,3-dihydro-3-[[4-[3-(1H-tetrazol-5-yl}phenyl]-2-pyridinyl]methyl]-2H-imidazol-2-one;
1-ethyl-1H-tetrazol-5-yl)-4-butyl-1,3-dihydro-3-[[4-[3-(1H-tetrazol-5-yl)phenyl]-2-pyridinyl]methyl]-2H-imidazol-2-one;
1-(1-propyl-1H-tetrazol-5-yl)-4-butyl-1,3-dihydro-3-[[4-[3-(1H-tetrazol-5-yl)phenyl]-2-pyridinyl]methyl]-2H-imidazol-2-one;
1-(1-isopropyl-1H-tetrazol-5-yl)-4-butyl-1,3-dihydro-3-[[4-[3-(1H-tetrazol-5-yl)phenyl]-2-pyridinyl]methyl]-2H-imidazol-2-one;
1-(1-butyl-1H-tetrazol-5-yl)-4-butyl-1,3 -dihydro-3-[[4-[3-(1H-tetrazol-5-yl)phenyl]-2-pyridinyl]methyl]-2H-imidazol-2-one;
1(1-secbutyl-1H-tetrazol-5-yl)-4-butyl-1,3-dihydro-3-[[4-[3-(1H-tetrazol-5-yl)phenyl]-2-pyridinyl]methyl]-2H-imidazol-2-one;
1-(1-isobutyl-1H-tetrazol-5-yl)-4-butyl-1,3-dihydro-3-[[4-[3-(1H-tetrazol-5-yl)phenyl]-2-pyridinyl]methyl]-2H-imidazol-2-one and
1-(1-tertbutyl-1H-tetrazol-5-yl)-4-butyl-1,3-dihydro-3-[[4-[3-(1H-tetrazol-5-yl)phenyl]-2-pyridinyl]methyl]-2H-imidazol-2-one.

Within this second group of compounds of Formula VII there is a fourth class of higher-interest compounds of Formula VII(d):

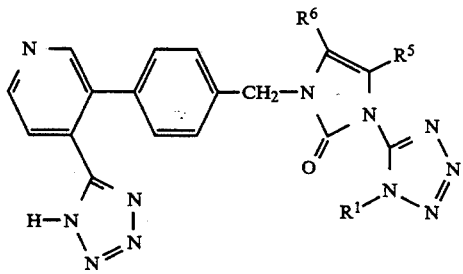

VII(d)

wherein R¹ is selected from hydrido, methyl, ethyl, n-propyl, isopropyl, n-butyl, tert-butyl, sec-butyl, isobutyl and n-pentyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII(d) consists of compounds and their stereoisomers and tautomers and the pharmaceutically-acceptable salts thereof, said compounds consisting of 1-(1-methyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-ethyl-1H-tetrazol-5-yl)-4-propyl-1,3-dihydro-3-[[4-[4-(1H-tetrazol-5-yl)phenyl]-3-pyridinyl]methyl]-2H-imidazol- 2-one;

1(1-propyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-isopropyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-butyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-secbutyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-isobutyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-tertbutyl-1H-tetrazol-5-yl)-4-propyl-1,3-dihydro-3-[[4-[4-(1H-tetrazol-5-yl)phenyl]-3-pyridinyl]methyl]-2H-imidazol-2-one;

1-(1-methyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-ethyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-propyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-isopropyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-butyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-secbutyl-1H-tetrazol-5-yl)-4-butyl-1,3-dihydro-3-[[4-[4-(1H-tetrazol-5-yl)phenyl]-3-pyridinyl]methyl]-2H-imidazol-2-one;

1-(1-isobutyl-1H-tetrazol-5-yl)-4-butyl-1,3-dihydro-3-[[4-[4-(1H-tetrazol-5-yl)phenyl]-3-pyridinyl]methyl]-2H-imidazol-2-one and 1-(1-tertbutyl-1H-tetrazol-5-yl)-4-butyl-1,3-dihydro-3-[[4-[4-(1H-tetrazol-5 -yl)phenyl]-3-pyridinyl]methyl]-2H-imidazol-2-one.

Within this second group of compounds of Formula VII there is a fifth class of higher-interest compounds of Formula VII(e):

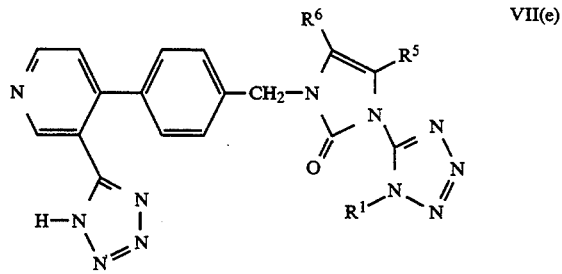

VII(e)

wherein R¹ is selected from hydrido, methyl, ethyl, n-propyl, isopropyl, n-butyl, tert-butyl, sec-butyl, isobutyl and n-pentyl; wherein R⁵ is hydrido; wherein R⁶ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII(e) consists of compounds and their stereoisomers and tautomers and the pharmaceutically-acceptable salts thereof, said compounds consisting of 1-(1-methyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

- (1-ethyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-propyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-isopropyl-1H-tetrazol-5-yl)-4-propyl-1,3-dihydro-3-[[4-[3 -(1H-tetrazol-5-yl)phenyl]-4-pyridinyl]methyl]-2H-imidazol-2-one;

1-(t-butyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-secbutyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-isobutyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-tertbutyl-1H-tetrazol-5-yl)-4-propyl-1,3-dihydro-3-[[4-[3-(1H-tetrazol-5-yl)phenyl]-4-pyridinyl]methyl]-2H-imidazol-2-one;

1-(1-methyl-1H-tetrazol-5-yl)-4-butyl-1,3-dihydro-3-[[4-[3-(1H-tetrazol-5-yl)phenyl]-4-pyridinyl]methyl]-2H-imidazol-2-one;

1-(1-ethyl-1H-tetrazol-5-yl)-4-butyl-1,3-dihydro-3-[[4-[3-(1H-tetrazol-5-yl)phenyl]-4-pyridinyl]methyl]-2H-imidazol-2-one;

1-(1-propyl-1H-tetrazol-5-yl)-4-butyl-1,3-dihydro-3-[[4-[3-(1H-tetrazol-5-yl)phenyl]-4-pyridinyl]methyl]-2H-imidazol-2-one;

1-(1-isopropyl-1H-tetrazol-5-yl)-4-butyl-1,3-dihydro-3-[[4-[3-(1H-tetrazol -5-yl) phenyl]-4-pyridinyl]methyl]-2H-imidazol-2-one;

1-(1-butyl-1H-tetrazol-5-yl)-4-butyl-1,3-dihydro-3-[[4-[3-(1H-tetrazol-5-yl)phenyl]-4-pyridinyl]methyl]-2H-imidazol-2-one;

1-(1-secbutyl-1H-tetrazol-5-yl)-4-butyl-1,3-dihydro-3-[[4-[3-(1H-tetrazol-5-yl)phenyl]-4-pyridinyl]methyl]-2H-imidazol-2-one;

1-(1-isobutyl-1H-tetrazol-5-yl)-4-butyl-1,3-dihydro-3-[[4-[3-(1H-tetrazol-5-yl)phenyl]-4-pyridinyl]methyl]-2H-imidazol-2-one and 1-(1-tertbutyl-1H-tetrazol-5-yl)-4-butyl-1,3-dihydro-3-[[4-[3-(1H-tetrazol-5-yl)phenyl]-4-pyridinyl]methyl]-2H-imidazol-2 -one.

Within this second group of compounds of Formula VII there is a sixth class of higher-interest compounds of Formula VII(f):

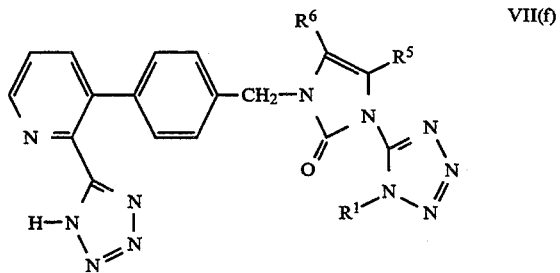

VII(f)

wherein $R^1$ is selected from hydrido, methyl, ethyl, n-propyl, isopropyl, n-butyl, tert-butyl, sec-butyl, isobutyl and n-pentyl; wherein $R^5$ is hydrido; wherein $R^6$ is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

A family of specific compounds of particular interest within Formula VII (f) consists of compounds and their stereoisomers and tautomers and the pharmaceutically-acceptable salts thereof, said compounds consisting of 1-(1-methyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-ethyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-propyl-1H-tetrazol-5-yl)-4-propyl-1,3-dihydro-3-[[4-[2-(1H-tetrazol-5 -yl)phenyl]-3-pyridinyl]methyl]-2H-imidazol-2-one;

1-(1-isopropyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-butyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-secbutyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-isobutyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-tertbutyl-1H-tetrazol-5-yl)-4-propyl-1,3-dihydro-3-[[4-[2-(1H-tetrazol-5-yl)phenyl]-3-pyridinyl]methyl]-2H-imidazol-2-one;

1-(1-methyl-1H-tetrazol-5-yl)-4-butyl-1,3-dihydro-3-[[4-[2-(1H-tetrazol-5-yl)phenyl]-3-pyridinyl]methyl]-2H-imidazol-2-one;

1-(1-ethyl-1H-tetrazol-5-yl)-4-butyl-1,3-dihydro-3-[[4-[2-(1H-tetrazol-5-yl)phenyl]-3-pyridinyl]methyl]-2H-imidazol-2-one;

1-(1-propyl-1H-tetrazol-5-yl)-4-butyl-1,3-dihydro-3-[[4-[2- (1H-tetrazol-5-yl)phenyl]-3-pyridinyl]-2H-imidazol-2-one;

1-(1-isopropyl-1H-tetrazol-5-yl)-4-butyl-1,3-dihydro-3-[[4-[2-(1H-tetrazol-5-yl)phenyl]-3-pyridinyl]methyl]-2H-imidazol-2-one;

1-(1-butyl-1H-tetrazol-5-yl)-4-butyl-1,3-dihydro-3-[[4-[2-(1H-tetrazol-5-yl)phenyl]-3-pyridinyl]methyl]-2H-imidazol-2-one;

1-(1-secbutyl-1H-tetrazol-5-yl)-4-butyl-1,3-dihydro-3-[[4-[2-(1H-tetrazol-5-yl)phenyl]-3-pyridinyl]methyl]-2H-imidazol-2-one;

1-(1-isobutyl-1H-tetrazol-5-yl)-4-butyl-1,3-dihydro-3-[[4-[2-(1H-tetrazol-5-yl)phenyl]-3-pyridinyl]methyl]-2H-imidazol-2-one and 1-(1-tertbutyl-1H-tetrazol-5-yl)-4-butyl-1,3-dihydro-3-[[4-[2-(1H-tetrazol-5-yl)phenyl]-3-pyridinyl]methyl]-2H-imidazol-2-one.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —$CH_2$— group. Where the term "alkyl" is used, either alone or within other terms such as "haloalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The terms "benzyl" and "phenylmethyl" are interchangeable. For any of the foregoing defined radicals, preferred radicals are those containing from one to about ten carbon atoms.

The term "arylheteroarylalkyl" embraces moieties, having an aryl fragment, a heteroaryl fragment and an alkyl fragment, of the type exemplified by moieties shown for the "A" substituent of Formula I, herein.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I-XXXV, wherein the R substituents are as defined for Formula I, above, except where further noted.

Scheme I

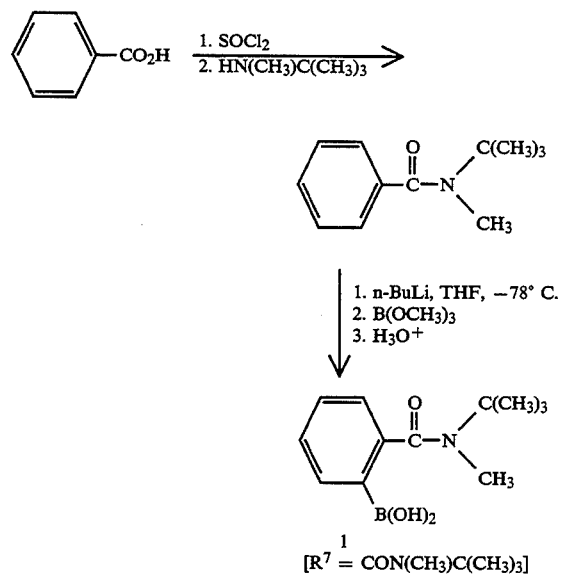

Synthetic Scheme I shows the preparation of the boronic acid 1 where $R^7$ equals N-tertbutyl-N-methylcarboxamide. In step 1, benzoic acid is treated with thionyl chloride to give the corresponding acid chloride which is subsequently reacted with N-tertbutyl-N-methylamine to give N-tertbutyl-N-methylbenzamide. In step 2, the amide is ortho-metalated and subsequently reacted with trimethyl borate. The free boronic acid 1 is produced on hydroylsis.

Scheme II

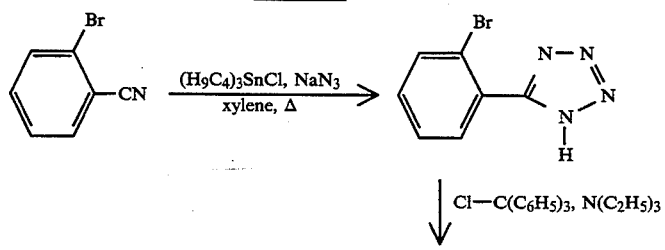

Scheme II

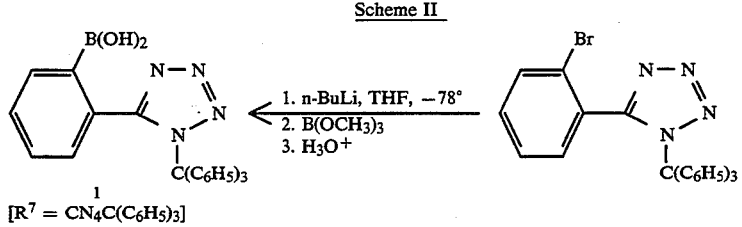

[R⁷ = CN₄C(C₆H₅)₃]

Synthetic Scheme II shows the preparation of the boronic acid 1 where $R^7$ equals N-triphenylmethyl-1H-tetrazole. In step 1, 2-bromobenzonitrile (Aldrich) is reacted with tributyltin azide to give the corresponding tetrazole. In step 2, the tetrazole is reacted with triphenylmethyl chloride in the presence of triethylamine to give the protected bromophenyltetrazole. In step 3, halogen-metal interchange with n-butyllithium generates the corresponding ortho-lithiated species which is reacted with trimethyl borate. The free boronic acid 1 is produced on hydrolysis.

Scheme III

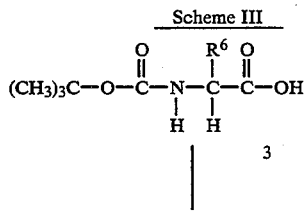

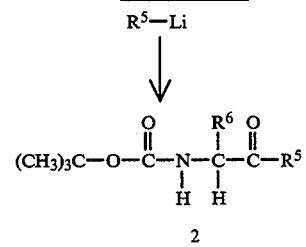

Synthetic Scheme III shows the preparation of N-Boc-amino ketones 2 (or aldehydes when $R^5=H$) from the corresponding N-Boc-amino acides 3. In step 1, the amino acid 3 is reacted with isobutyl chloroformate in the presence of triethylamine and subsequently with N,O-dimethylhydroxylamine to give the corresponding N-methoxy-N-methylamide 4. In step 2, the amide 4 is reacted with an organolithium reagent $R^5$-Li (or lithium aluminum hydride (LAH) when $R^5=H$) to give the desired ketone 2 (or aldehyde when $R^5=H$).

Scheme IV

METHOD A:

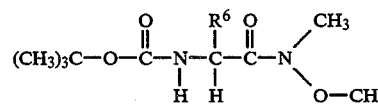

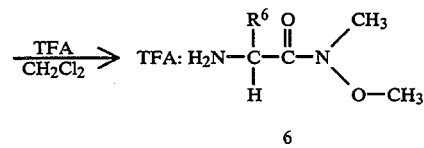

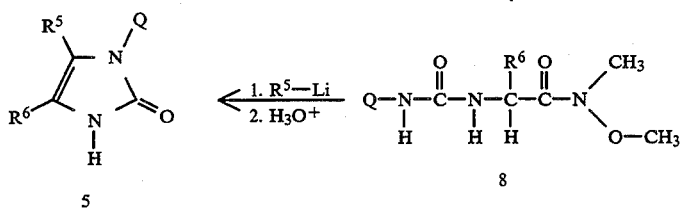

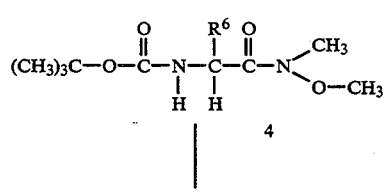

Synthetic Scheme IV shows the preparation of imidazol-2-ones 5 from the corresponding amides 4 via Method A. In step 1, the protected amide 4 (prepared in Scheme III) is reacted with trifluoroacetic acid (TFA) to give the TFA salt 6 of the free amine. In step 2, the salt 6 is reacted with the appropriate isocyanate 7 in the presence of triethylamine to give the urea 8. In step 3, the urea 8 is reacted with an organolithium reagent $R^5$-Li (or lithium aluminum hydride (LAH) when $R^5=H$) and subsequently cyclized to the imidazole-2-one 5 on treatment with dilute acid during the work-up procedure.

Scheme V

METHOD B:

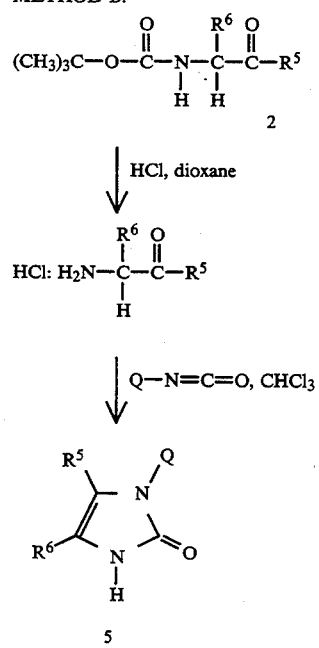

Synthetic Scheme V shows the preparation of imidazol-2-ones 5 from the corresponding N-Boc-protected amino ketones 2 (or aldehydes when $R^5=H$) via Method B. In step 1, the carbonyl compound 2 (prepared in Scheme III) is reacted with anhydrous hydrogen chloride in dioxane to give the HCl salt 9. In step 2, the salt 9 is reacted with the appropriate isocyanate 7 in chloroform to give the imidazol-2-one 5 directly.

Scheme VI

METHOD C:

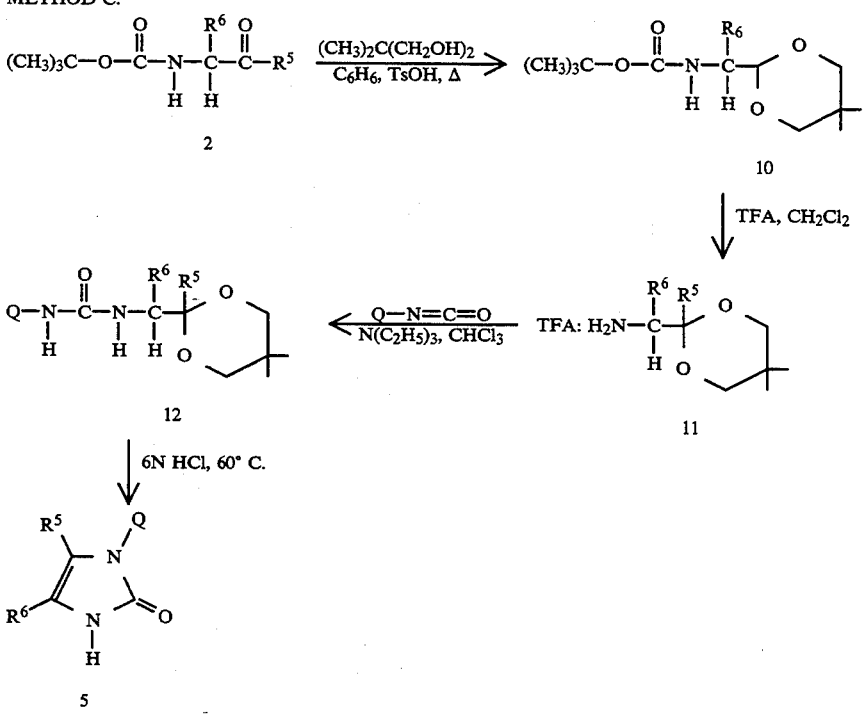

Synthetic Scheme VI shows the preparation of imidazol-2-ones 5 from the corresponding N-Boc-protected amino ketones 2 (or aldehydes when $R^5=H$) via Method C. In step 1, the carbonyl compound 2 (prepared in Scheme III) is reacted with 2,2-dimethyl-1,3-propandiol to give the cyclic ketal 10. In step 2, the ketal 10 is reacted with TFA to give the TFA salt 11 of the free amine. In step 3, the salt 11 is reacted with the appropriate isocyanate 7 in the presence of triethylamine to give the urea ketal 12. In step 4, the urea ketal 12 is reacted with 6N hydrochloric acid at 60° C. to give the desired imidazol-2-one 5 directly.

Scheme VII

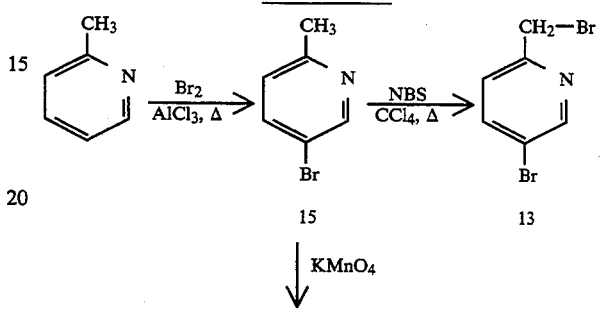

-continued
Scheme VII

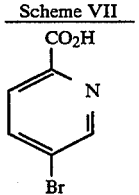

16

1. Cl—CO—OCH₂CH(CH₃)₂
   N(C₂H₅)₃, CH₂Cl₂, 0° C.
2. HN(CH₃)OCH₃
3. LAH

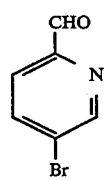

14

Synthetic Scheme VII shows the preparation of 2-bromomethyl-5-bromopyridine (13) and 5-bromo-2-pyridinecarboxaldehyde (14) from 2-picoline (Aldrich). In step 1, 2-picoline is reacted with bromine in the presence of a large excess of aluminum chloride at elevated temperatures to give 5-bromo-2-picoline (15). In step 2a, 15 is reacted with NBS to give the 2-pyridinylmethyl bromide 13. In step 2b, the intermediate 15 is treated with potassium permanganate to give the corresponding picolinic acid 16. In step 3b, the acid 16 is first converted to its N-methoxy-N-methylamide and subsequently reduced with LAH to provide 5-bromo-2-pyridinecarboxaldehyde (14).

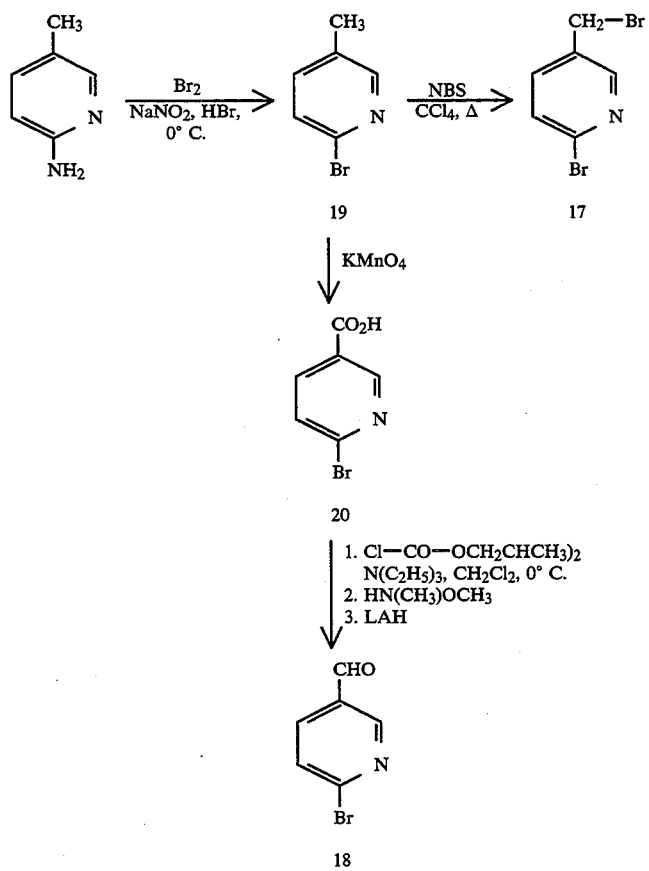

Synthetic Scheme VIII shows the preparation of 2-bromo-5-bromomethylpyridine (17) and 2-bromo-5-pyridinecarboxaldehyde (18) from 2-amino-5-picoline (Aldrich). In step 1, 2-amino-5-picoline is reacted with bromine in the presence of hydrobromic acid and sodium nitrite at 0° C. to give 2-bromo-5-picoline (19). In step 2a, 19 is reacted with NBS to give the 3-pyridinylmethyl bromide 17. In step 2b, the intermediate 19 is treated with potassium permanganate to give the corresponding nicotinic acid 29. In step 3b, the acid 20 is first converted to its N-methoxy-N-methylamide and subsequently reduced with LAH to provide 2-bromo-5-pyridinecarboxaldehyde (18).

Scheme IX

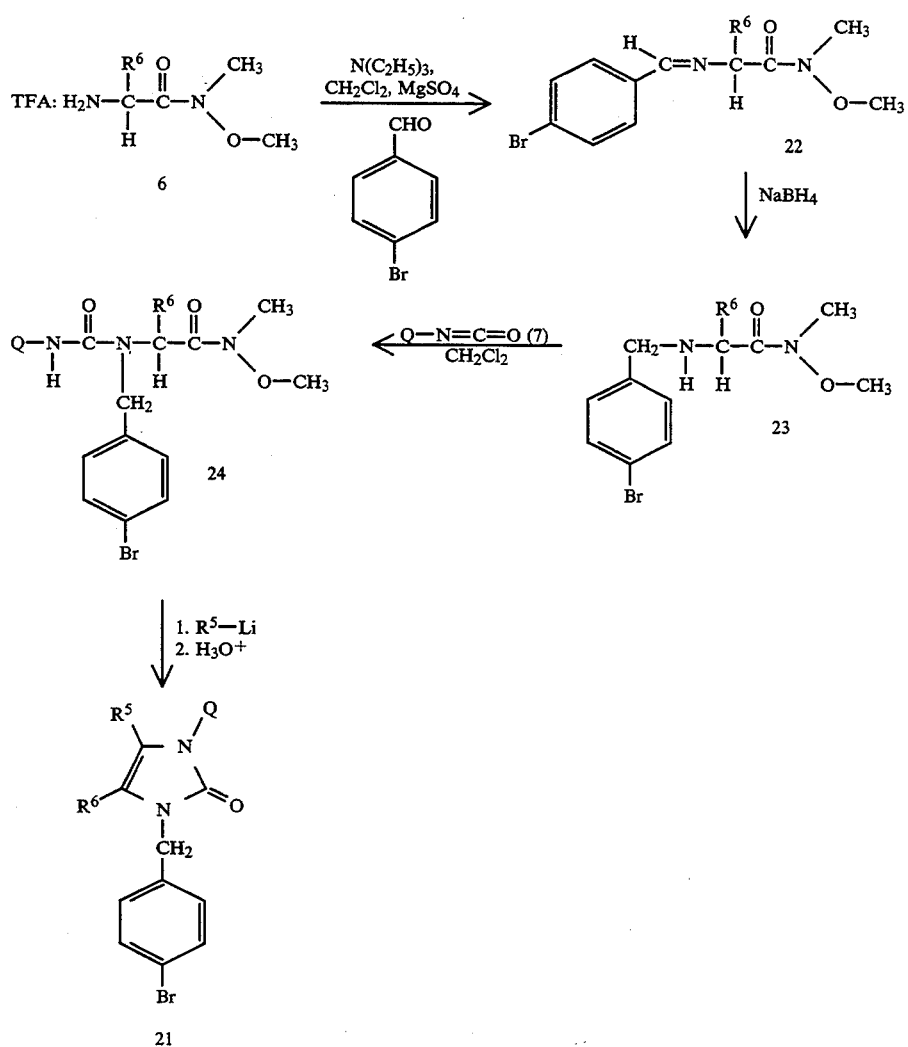

Synthetic Scheme IX shows the preparation of (4-bromobenzyl)imidazol-2-ones 21 from the TFA salt of the amino amide 6 (prepared in Scheme III). In step 1, the TFA salt 6 is allowed to react with the 4-bromobenzaldehyde in the presence of triethylamine and anhydrous magnesium sulfate to give the imine 22. In step 2, the imine 22 is allowed to react with sodium borohydride to give the substituted benzylamine 23. In step 3, the benzylamine 23 is allowed to react with the appropriate isocyanate 7 to give the substituted benzylurea 24. In step 4, the urea 24 is first allowed to react with an organolithium reagent $R^5$-Li (or lithium aluminum hydride (LAH) when $R^5$=H) and subsequently with dilute aqueous acid to give the desired 3-(4-bromobenzyl)imidazol-2-ones.

Scheme X

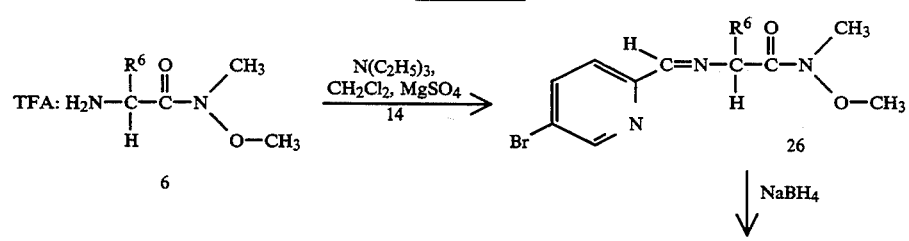

Scheme X

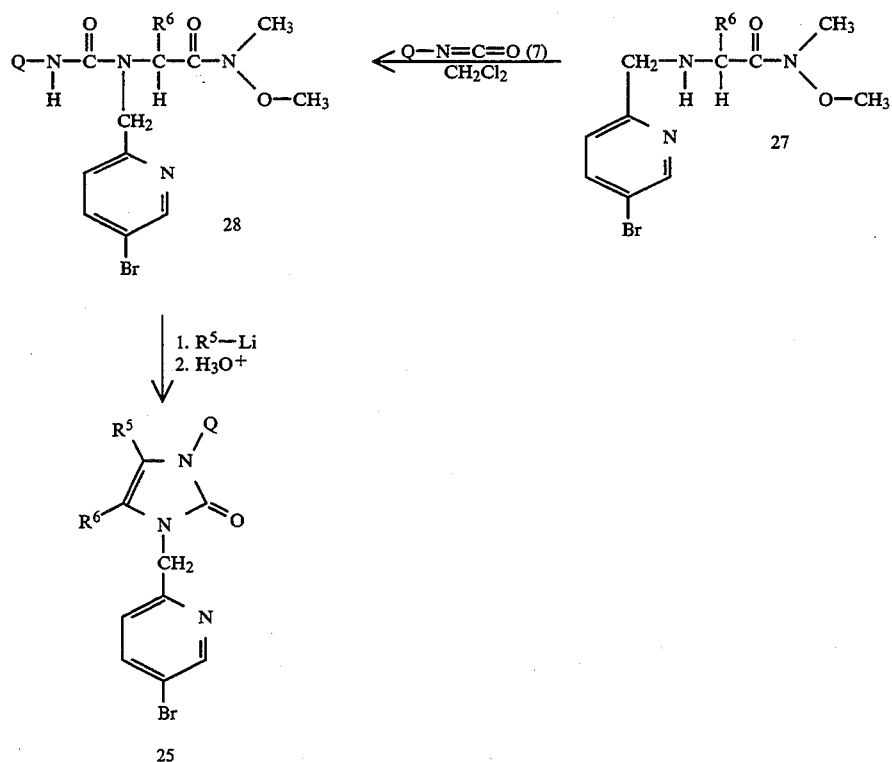

Synthetic Scheme X shows the preparation of 3-(5-bromo-2-pyridinylmethyl)imidazol-2-ones 25 from the TFA salt of the amino amide 6 (prepared in Scheme III). In step 1, the TFA salt 6 is allowed to react with the 5-bromo-2-pyridinylaldehyde 14 (prepared in Scheme VII) in the presence of triethylamine and anhydrous magnesium sulfate to give the imine 26. In step 2, the imine 26 is allowed to react with sodium borohydride to give the substituted benzylamine 27. In step 3, the benzylamine 27 is allowed to react with the appropriate isocyanate 7 to give the substituted benzylurea 28. In step 4, the urea 28 is first allowed to react with an organolithium reagent $R^5$-Li (or lithium aluminum hydride (LAH) when $R^5$=H) and subsequently with dilute aqueous acid to give the desired 3-(5-bromo-2-pyridinylmethyl)imidazol-2-ones 25.

Scheme XI

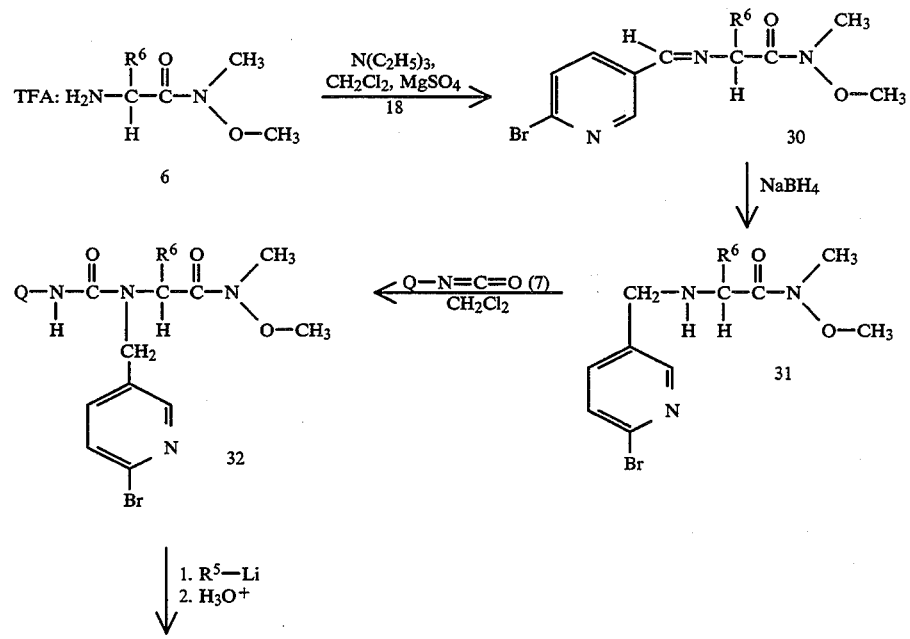

Scheme XI

-continued

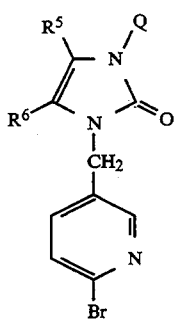

29

Synthetic Scheme XI shows the preparation of 3-(2-bromo-5-pyridinylmethyl)imidazol-2-ones 29 from the TFA salt of the amino amide 6 (prepared in Scheme III). In step 1, the TFA salt 6 is allowed to react with 2-bromo-5-pyridinylaldehyde 18 (prepared in Scheme VIII) in the presence of triethylamine and anhydrous magnesium sulfate to give the imine 30. In step 2, the imine 30 is allowed to react with sodium borohydride to give the substituted benzylamine 31. In step 3, the benzylamine 31 is allowed to react with the appropriate isocyanate 7 to give the substituted benzylurea 32. In step 4, the urea 32 is first allowed to react with an organolithium reagent $R^5$-Li (or lithium aluminum hydride (LAH) when $R^5$=H) and subsequently with dilute aqueous acid to give the desired 3-(2-bromo-5-pyridinylmethyl)imidazol-2-ones 29.

pyridinylmethyl)imidazol-2-ones 29 from the parent imidazol-2-ones 5 (prepared in Scheme IV, Scheme V, or Scheme VI). The imidazol-2-one 5 is first treated with a base, such as potassium t-butoxide, and subsequently with the alkylating agent 4-bromobenzyl bromide, 13 (prepared in Scheme VII), and 17 (prepared in Scheme VIII) to give 3-(4-bromobenzyl)imidazol-2-ones 21, 3-(5-bromo-2-pyridinylmethyl)imidazol-2-ones 25, and 3-(2-bromo-5-pyridinylmethyl)imidazol-2-ones 29, respectively.

Scheme XII

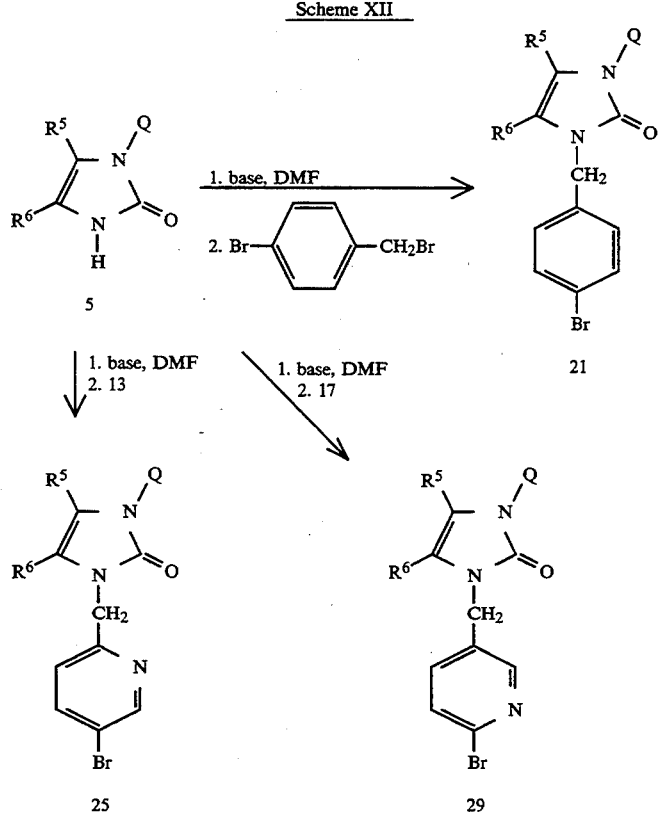

Synthetic Scheme XII shows the preparation of 3-(4-bromobenzyl) imidazol-2-ones 21, 3-(5-bromo-2-pyridinylmethyl)imidazol-2-ones 2.5, and 3-(2-bromo-5-

Scheme XIII

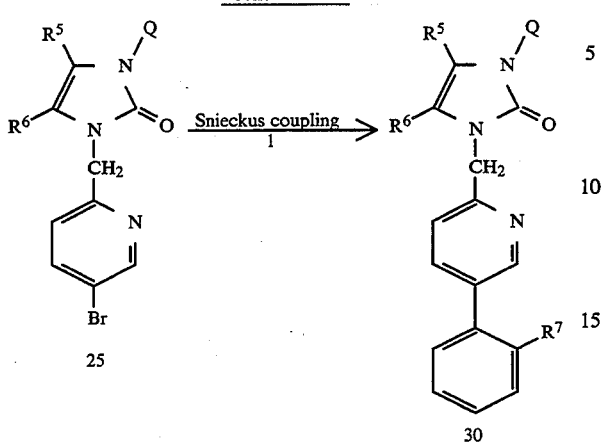

Synthetic Scheme XIII shows the preparation of 3-[[5-[2-(1H-tetrazol-5-yl)phenyl]-2-pyridinyl]methyl]-2H-imidazol-2-ones 30 from the boronic acid 1 (prepared in Scheme I and Scheme II) and the bromoimidazol-2-one coupling reagent 25 (prepared in Scheme X and Scheme XII). The boronic acid 1 is reacted with the bromoimidazol-2-one coupling reagent 25 in the presence of a palladium zero catalyst via a Snieckus coupling [see M. J. Sharp and V. Snieckus, *Tetrahedron Lett.*, 5997(1985)] to give the angiotensin II antagonists 30 of this invention.

Scheme XIV

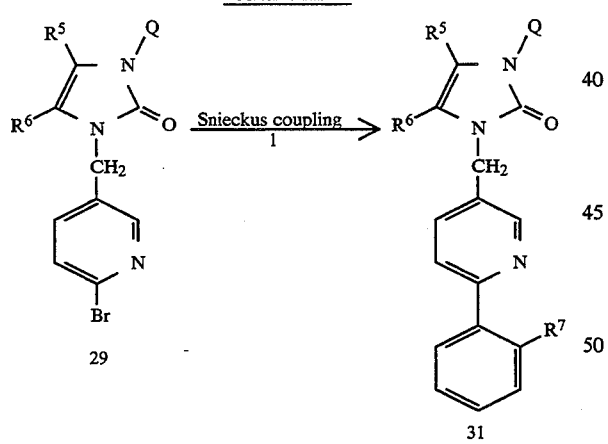

Synthetic Scheme XIV shows the preparation of 3-[[6-[2-{1H-tetrzol-5-yl)phenyl]-3-pyridinyl]methyl]-2H-imidazol-2-ones 31 from the boronic acid 1 (prepared in Scheme I and Scheme II) and the bromoimidazol-2-one coupling reagent 29 (prepared in Scheme XI and Scheme XII). The boronic acid 1 is reacted with the bromoimidazol-2-one coupling reagent 29. in the presence of a palladium zero catalyst via a Snieckus coupling [see M. J. Sharp and V. Snieckus, *Tetrahedron Lett.*, 5997(1985)] to give the angiotensin II antagonists 31 of this invention.

Scheme XV

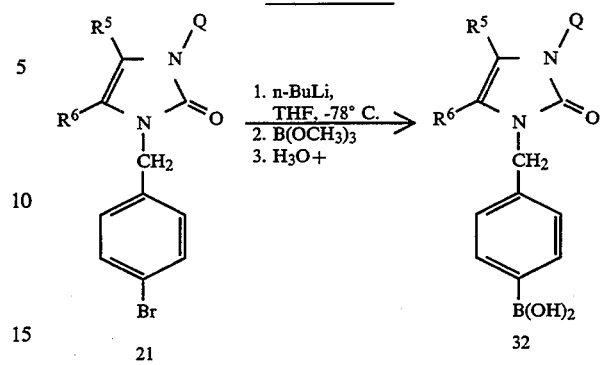

Synthetic Scheme XV shows the preparation of the imidazol-2-one boronic acid coupling reagents 32 from the corresponding 3-(4-bromobenzyl)imidazol-2-ones 21 (prepared in Scheme IX and Scheme XII). Halogen-metal interchange generates the corresponding lithiated species from 21. which is reacted with trimethyl borate. The free imidazol-2-one boronic acid coupling reagents 32 are produced on acid hydrolysis.

Scheme XVI

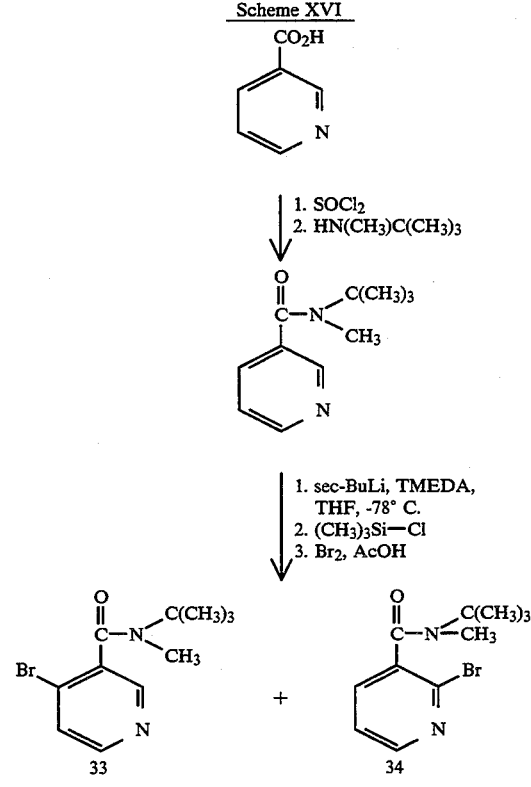

Synthetic Scheme XVI shows the preparation of the 4-bromopyridine coupling reagent 33 [$R^7$=CON(CH$_3$)C(CH$_3$)$_3$] and the 2-bromopyridine coupling reagent 34 [$R^7$=CON(CH$_3$)C(CH$_3$)$_3$] from nicotinic acid. In step 1, N-tertbutyl-N-methylnicotinamide is prepared from nicotinoyl chloride and N-tertbutyl-N-methylamine. In step 2, ortho-metalalion with sec-butyllithium gives a mixture of regioanions which are reacted with trimethylsilyl chloride; subsequent conversion to the corresponding bromides on treatment with bromine in acetic acid and separation of the regioisomers by chromatography provides 33 and 34.

Scheme XVII

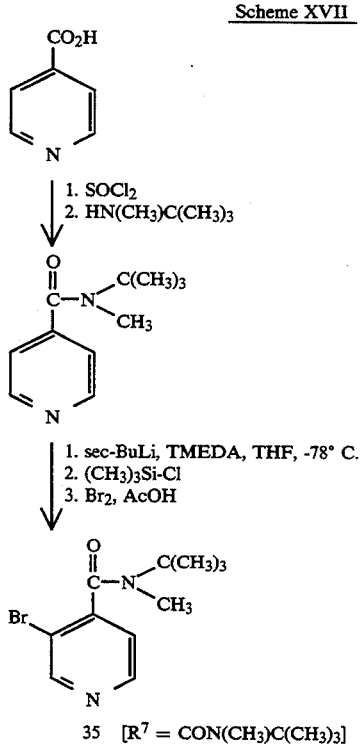

35 [R⁷ = CON(CH₃)C(CH₃)₃]

Scheme XVIII

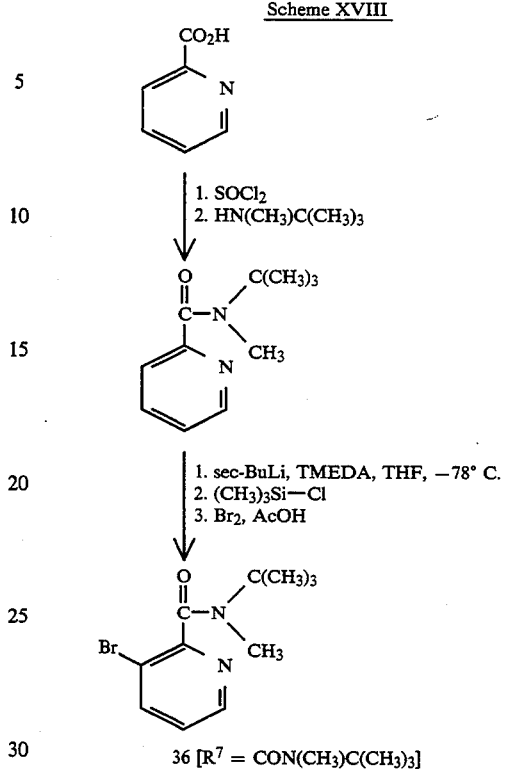

36 [R⁷ = CON(CH₃)C(CH₃)₃]

Synthetic Scheme XVII shows the preparation of the 3-bromopyridine coupling reagent 35 [R⁷=CON(CH₃)C(CH₃)₃] from isonicotinic acid. In step 1, N-tertbutyl-N-methylisonicotinamide is prepared from isonicotinoyl chloride and N-tertbutyl-N-methylamine. In step 2, reaction with sec-butyllithium gives the ortho-lithiated species which is reacted with trimethylsilyl chloride and subsequently converted to the corresponding bromide 35 on treatment with bromine in acetic acid.

Synthetic Scheme XVIII shows the preparation of the 3-bromopyridine coupling reagent 36 [R⁷=CON(CH₃)C(CH₃)₃] from picolinic acid. In step 1, N-tertbutyl-N-methylpicolinamide is prepared from picolinoyl chloride and N-tertbutyl-N-methylamine. In step 2, reaction with sec-butyllithium gives the ortho-lithiated species which is reacted with trimethylsilyl chloride and subsequently converted to the corresponding bromide 36 on treatment with bromine in acetic acid.

Scheme XIX

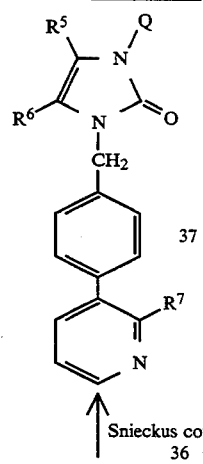

Snieckus coupling
36

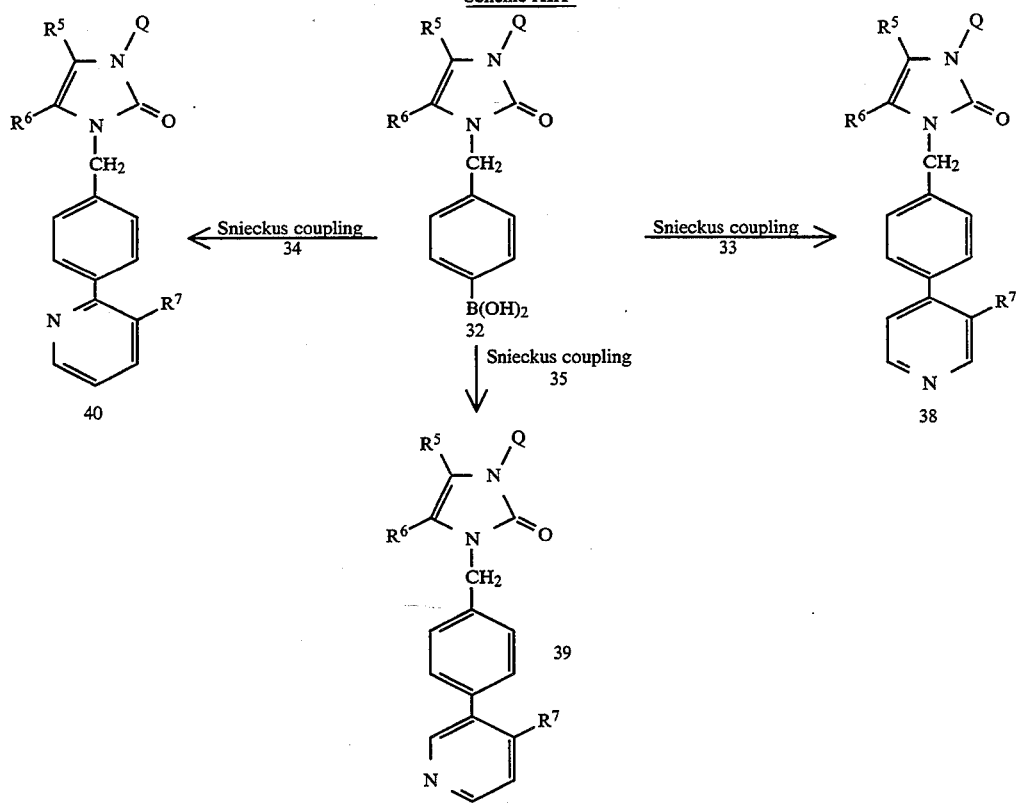

Synthetic Scheme XIX shows the preparation of 3-(pyridinylbenzyl)imidazol-2-ones 37, 38, 39 and 40 from the common imidazol-2-one boronic acids 32 (Scheme XV) and the corresponding bromo coupling reagents 36 (Scheme XVIII), 33 (Scheme XVI, 35 (Scheme XVII), and 34 (Scheme XVI), respectively. The boronic acids 32 are reacted with the bromo coupling reagents 36, 33, 35 and 34 in the presence of a palladium zero catalyst via a Snieckus coupling [see M. J. Sharp and V. Snieckus, *Tetrahedron Lett.*, 5997 (1985)] to give the angiotensin II antagonists 37, 38, 39 and 40, respectively, of this invention.

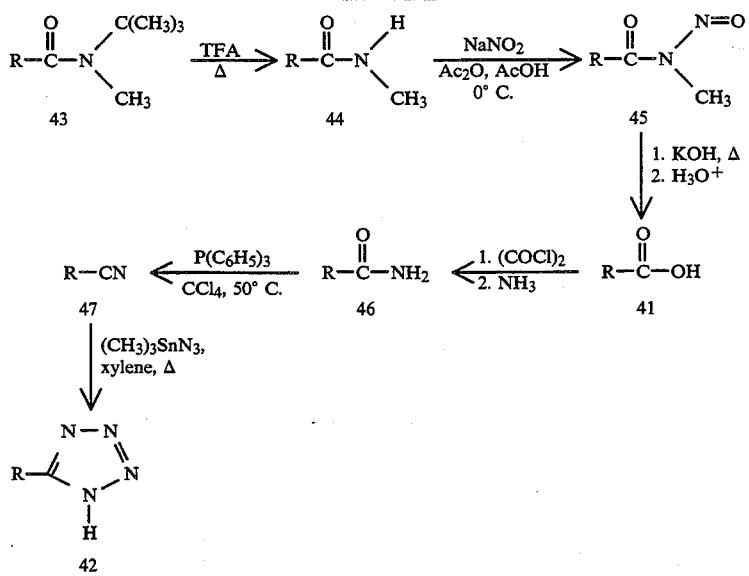

Synthetic Scheme XX shows the preparation of carboxylic acid analogs 41 and 1H-tetrazole analogs 42 from analogs which have $R^7 = CON(CH_3)C(CH_3)_3$. In step 1, the N-tertbutyl-N-methylamide analog 43 is reacted with trifluoroacetic acid at reflux to give the N-methylamide 44. In step 2, the N-methylamide 44 is reacted with sodium nitrite in acetic anhydride/acetic acid at 0° C. to give the corresponding N-methyl-N-nitrosoamide 45. In step 3, the N-methyl-N-nitrosoamide 45 is hydrolyzed in base to give the corresponding carboxylic acid angiotensin II antagonists of this invention. In step 4, the acid analog 41 is reacted with oxalyl chloride and subsequently with anhydrous ammonia to give the primary amide 46. In step 5, the amide 46 is reacted with triphenylphosphine in carbon tetrachloride at 50° C. to give the corresponding nitrile 47. In step 6, the nitrile 47 is reacted with trimethyltin azide in xylene at reflux to provide the 1H-tetrazole angiotensin II antagonists of this invention.

Scheme XXI

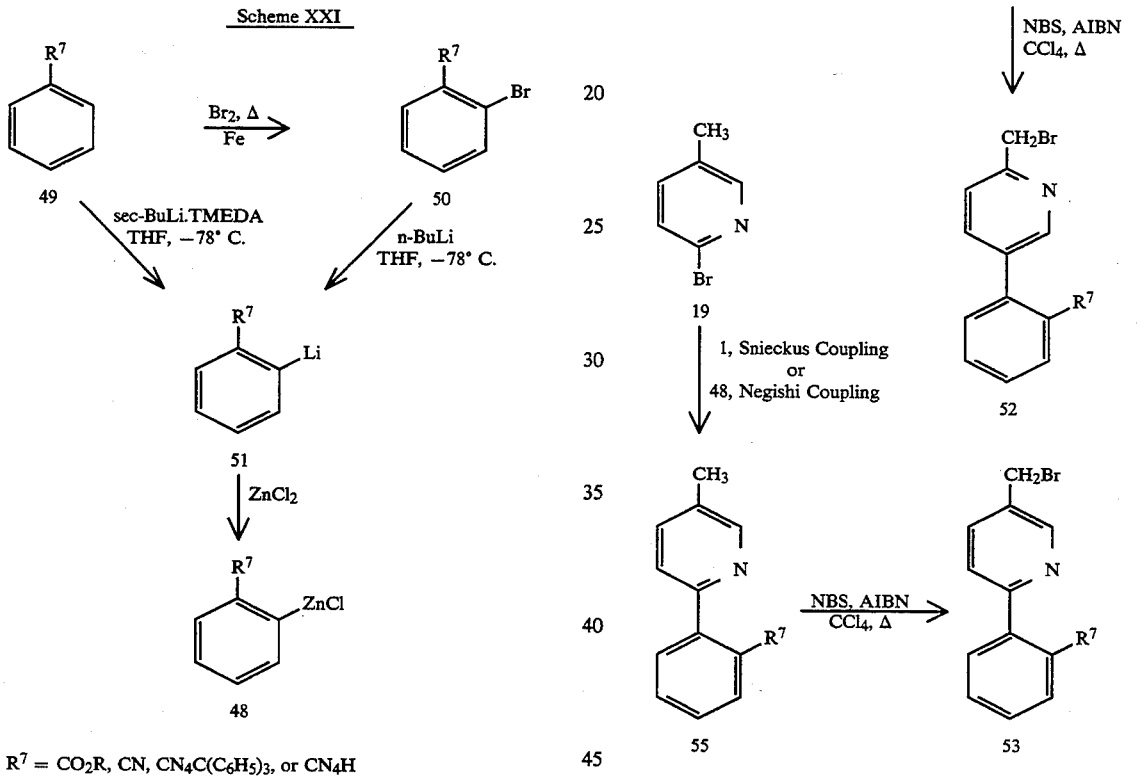

$R^7 = CO_2R$, CN, $CN_4C(C_6H_5)_3$, or $CN_4H$

Synthetic Scheme XXI shows the preparation of the organozinc reagent 48 from the appropriate benzoic acid analog 49. In step 1, the analog 49 is brominated with bromine in the presence of a suitable catalyst, e.g., iron, to give the 2-bromo analog 50. In step 2, the 2-bromo analog 50 was converted to the organolithium reagent 51 by reaction with n-butyllithium in THF at −78° C., a process known as halogen-metal interchange. Alternatively, the organolithium reagent 51 can be generated directly by the reaction of 49 with an alkyllithium reagent in the presence or absence of a suitable complexing agent in THF at −78° C., e.g., sec-butyllithium/TMEDA (N,N,N',N'-tetramethylethylenediamine). In step 3, the organolithium reagent 51 was treated with anhydrous zinc chloride at −78° C. and subsequently allowed to warm to ambient temperature. The organozinc reagent 48 was generated and used in situ.

Synthetic Scheme XXII shows the preparation of the 2-pyridinyl alkylating reagent 52 and the 3-pyridinyl alkylating 53 from 15 (Scheme VII) and 19 (Scheme VIII), respectively. In step 1, 15 and 19 were coupled with 1 using Snieckus conditions (Scheme XIII) or 48 using Negishi conditions [see E. Negishi, A. O. King, and N. Okukado, J. Org. Chem., 42, 1821 (1977)] to give 54 and 55, respectively. In step 2, the coupled biaryl compounds 54 and 55 were brominated using NBS/AIBN to give the 2-pyridinyl alkylating reagent 52 and the 3-pyridinyl alkylating reagent 53, respectively.

Scheme XXIII

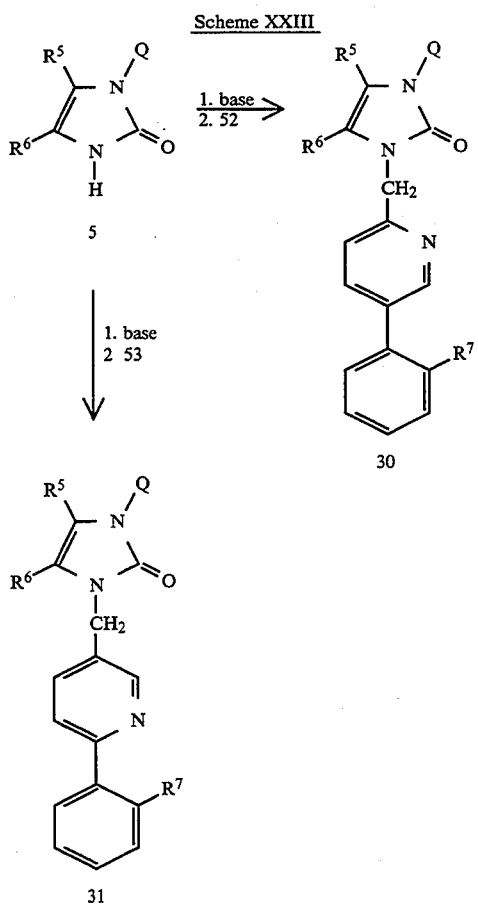

Synthetic Scheme XXIII shows the preparation of 3-[[5-[2-(1H-tetrazol-5-yl)phenyl]-2-pyridinyl]methyl]-2H-imidazol-2-ones 30 ($R^7$=CN$_4$H) and 3-[[6-[2-(1H-tetrazol-5-yl)phenyl]-3-pyridinyl]methyl]-2H-imidazol-2-ones 31. ($R^7$=CN$_4$H) from the parent imidazol-2-ones 5 (prepared in Scheme IV, Scheme V, or Scheme VI). The imidazol-2-one 5 was first treated with a base, such as potassium t-butoxide, and subsequently with the alkylating reagent 52 or 53 (Scheme XXII) to give 3-[[5-[2-(1H-tetrazol-5-yl)phenyl]-2-pyridinyl]methyl]-2H-imidazol-2-ones 30 ($R^7$=CN$_4$H) and 3-[[6-[2-(1H-tetrazol-5-yl)phenyl]-3-pyridinyl]methyl]-2H-imidazol-2-ones 31. ($R^7$=CN$_4$H), respectively.

Scheme XXIV

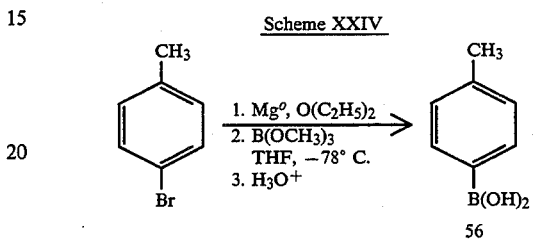

Synthetic Scheme XXIV shows the preparation of 4-methylphenylboronic acid (56) from 4-bromotoluene. In step 1, the Grignard reagent was generated by the reaction of 4-bromotoluene with metallic magnesium in ether at reflux. In step 2, a THF solution of trimethoxyborane was cooled to −78° C. and slowly treated with the Grignard reagent. In step 3, the boronic ester was hydrolyzed with aqueous hydrochloric acid to give 4-methylphenylboronic acid (56).

Scheme XXV

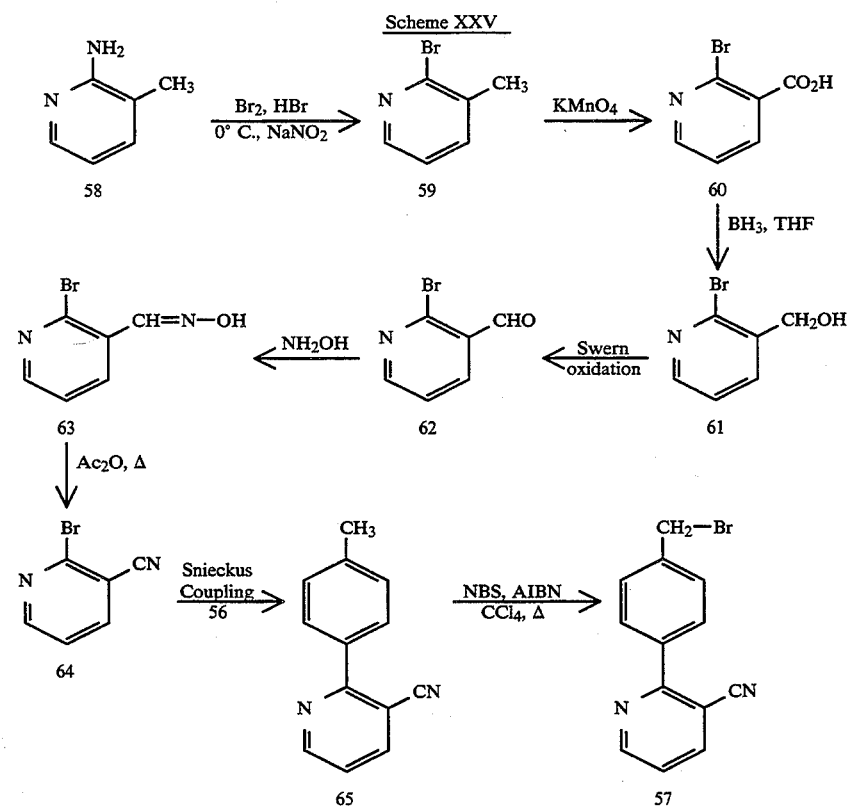

Synthetic Scheme XXV shows the 8-step preparation of the alkylating reagent 2-(4-bromomethylphenyl)-3-cyanopyridine (57) from 2-amino-3-cyanopyridine (58) (Aldrich). In step 1, the aminopicoline 58 was converted to the bromopicoline 59 by reaction with bromine, concentrated hydrobromic acid, and sodium nitrite at 0° C. In step 2, the picoline 59 was oxidized with $KMNO_4$ to give the corresponding carboxylic acid 60. In step 3, the acid 60 was reduced to the alcohol 61 with borane/THF. In step 4, the alcohol 61 was oxidized to the aldelyde 62 under Swern conditions or by using $MnO_2$. In step 5, the aldehyde 62 was reacted with hydroxylamine to give the oxime 63. In step 6, the oxime 63 was converted to 2-bromo-3-cyanopyridine (64) with acetic anhydride at reflux. In step 7, the nitrile 64 was coupled with 4-methylphenylboronic acid (56) (Scheme XXIV) using Snieckus conditions (Scheme XIII) to give 3-cyano-2-(4-methylphenyl)pyridine (65). In step 8, 65 was brominated with NBS/AIBN in carbon tetrachloride at reflux to give the desired alkylating reagent 57.

treated with condensed ammonia to give the amide 70. In step 4, the amide 70 was converted to 3-bromo-4-cyanopyridine (71) by treatment with $P_2O_5$ at high temperatures. In step 5, the nitrile 71 was coupled with 4-methylphenylboronic acid (56) (Scheme XXIV) using Snieckus conditions (Scheme XIII) to give 4-cyano-3-(4-methylphenyl)pyridine (72). In step 6, 72 was brominated with NBS/AIBN in carbon tetrachloride at reflux to give the desired alkylating reagent 66.

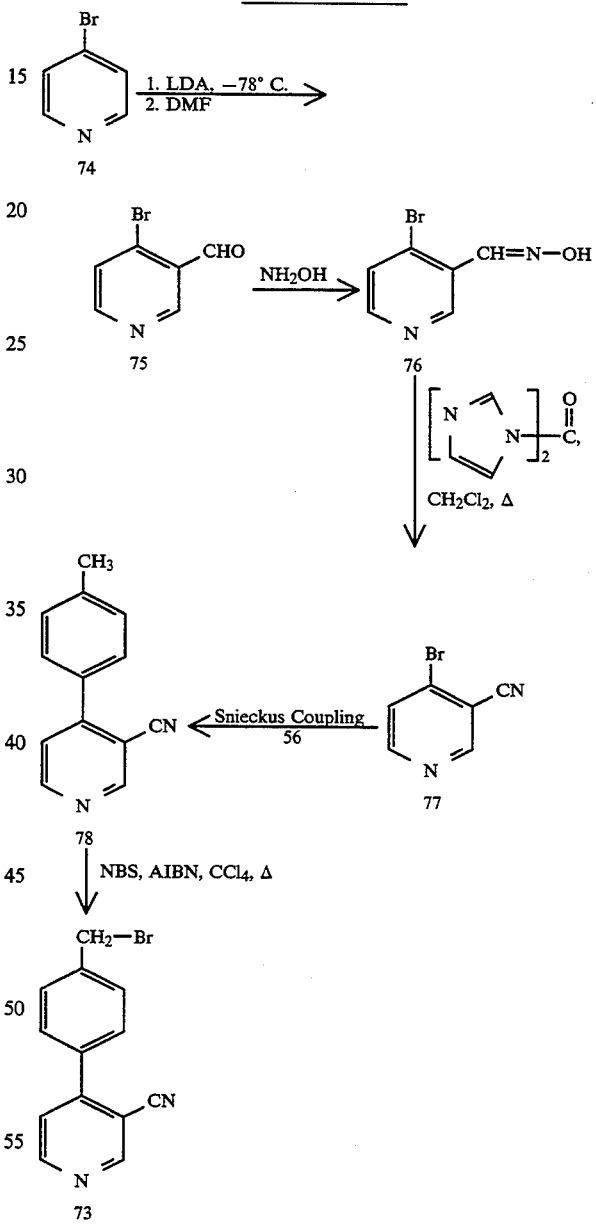

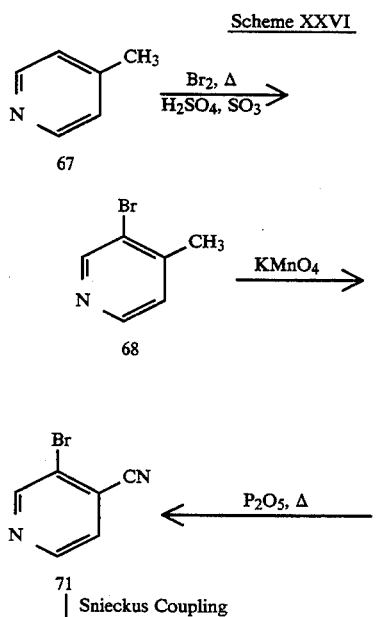

Synthetic Scheme XXVI shows the 6-step preparation of the alkylating reagent 3-(4-bromomethylphenyl)-4-cyanopyridine (66) from 4-picoline (67) (Aldrich). In step 1, 4-picoline was brominated with bromine in fuming sulfuric acid at high temperatures to give 3-bromo-4-picotine (68). In step 2, the picoline 68 was oxidized to the corresponding carboxylic acid 69 with $KMnO_4$. In step 3, the acid 69 was first converted to its acid chloride with oxalyl chloride and subsequently Synthetic Scheme XXVII shows the 5-step preparation of the alkylating reagent 4-(4-bromomethylphenyl)-3-cyanopyridine (73) from 4-bromopyridine (74) (Aldrich). In step 1, the ortho-bromo carbanion was generated with LDA in THF at −78° C. and reacted with anhydrous DMF to give 4-bromo-3-carboxaldehyde 75. In step 2, the aldehyde 75 was reacted with hydroxylamine to give the oxime 76. In step 3, the oxime 76 was dehydrated with 1,1′-carbonyldiimidazole in methylene chloride at reflux to give 4-bromo-3-cyanopyridine (77). In step 4, the nitrile 77 was coupled with 4-methylphenylboronic acid (56) (Scheme XXIV) using Snieckus conditions (Scheme XIII) to give 3-cyano-4-(4-methylphenyl)pridine (78). In step 5, 78 was brominated with NBS/AIBN in carbon tetrachloride at reflux to give the desired alkylating reagent 73.

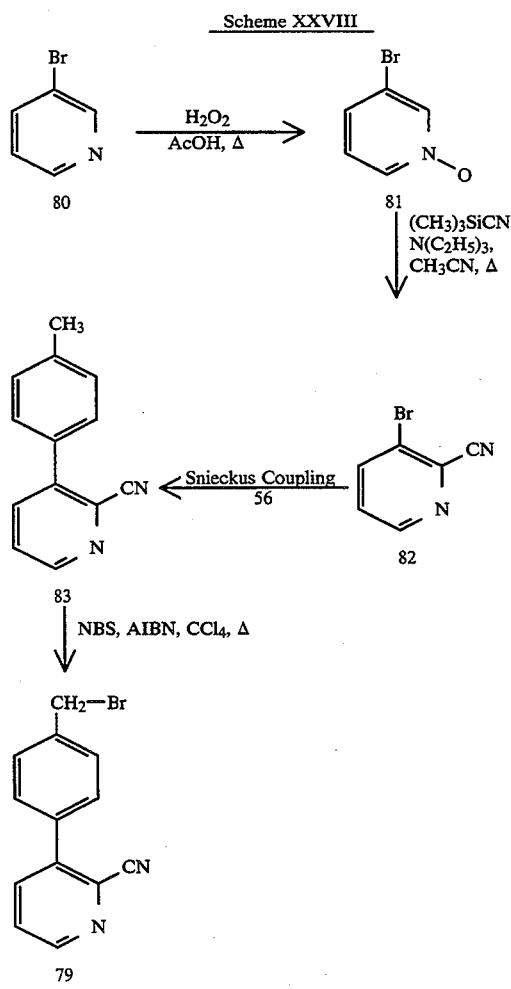

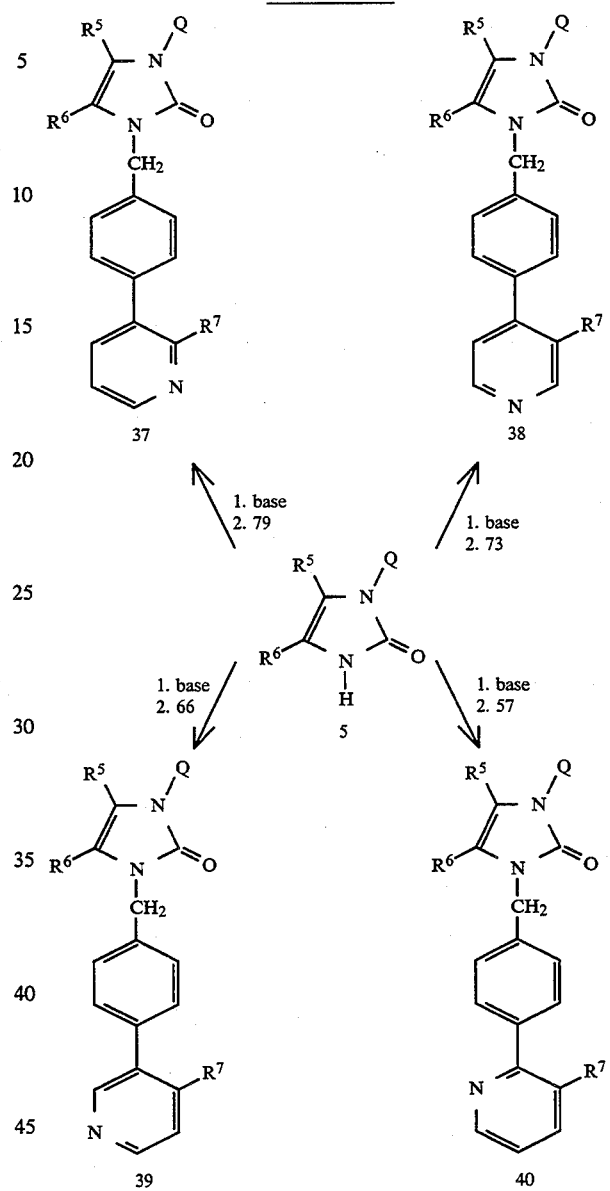

Synthetic Scheme XXVIII shows the 4-step preparation of the alkylating reagent 2-cyano-3-(4-bromomethylphenyl)pyridine (79) from 3-bromopyridine (80) (Aldrich). In step 1, the pyridine 80 was reacted with hydrogen peroxide in acetic acid at reflux to give the pyridine N-oxide 81. In step 2, the N-oxide 81 was converted to 3-bromo-2-cyanopyridine (82) by reaction with trimethysilylcyanide and triethyl anine in acetonitrile at reflux. In step 3, the nitrile 82 was coupled with 4-methylphenylboronic acid (56) (Scheme XXIV) using Snieckus conditions (Scheme XIII) to give 2-cyano-3-(4-methylphenyl) pyridine (83). In step 4, 83 was brominated with NBS/AIBN in carbon tetrachloride at reflux to give the desired alkylating reagent 79.

Synthetic Scheme XXIX shows the preparation of 1,4,5-trisubstituted-1,3-dihydro-3-[[4-(2-cyano-3-pyridinyl)phenyl]methyl]-2H-imidazol-2-ones 37 ($R^7$=CN), 1,4,5-trisubstituted-1,3-dihydro-3-[[4-(3-cyano-4-pyridinyl)phenyl]methyl]-2H-imidazol-2-ones 38 ($R^7$=CN), 1,4,5-trisubstituted-1,3-dihydro-3-[[4-(4-cyano-3-pyridinyl)phenyl]methyl]-2H-imidazol-2-ones 39 ($R^7$=CN), and 1,4,5-trisubstituted-1,3,-dihydro-3-[[4-(3-cyano-2-pyridinyl)phenyl]methyl]-2H-imidazol-2-ones 40 ($R^7$=CN) from the parent 1,4,5-trisubstituted-1,3-dihydro-2H-imidazol-2-ones 5 (prepared in Scheme IV, Scheme V, or Scheme VI). The imidazol-2-one 5 was first treated with a base, such as potassium t-butoxide, and subsequently with the alkylating reagents 79 (Scheme XXVIII), 73 (Scheme XXVII), 66 (Scheme XXVI), and 57 (Scheme XXV) to give the alkylated products 37 ($R^7$=CN), 38 ($R^7$=CN, 39 ($R^7$=CN), and 40 ($R^7$=CN), respectively.

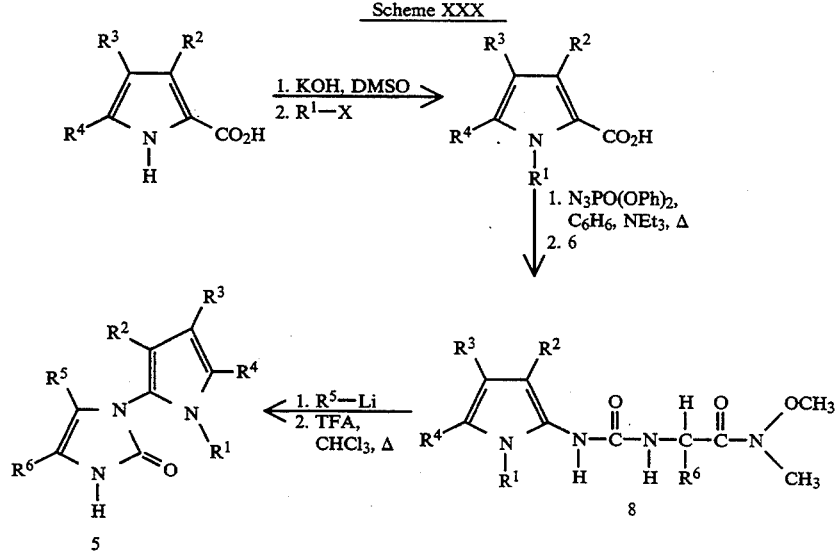

Synthetic Scheme XXX shows the preparation of the 1-(1H-pyrrol-2-yl)imidazol-2-ones 5 from the corresponding commercially available pyrrole-2-carboxylic acids. In Step 1, the N-substituted pyrrole is generated under basic conditions. In Step 2, the acid is converted to its corresponding isocyanate via a Curtius rearrangement and reacted in situ with the aminoamide 6 (Scheme IV) to give the urea 8. In Step 3, the urea is reacted with an organolithium reagent $R^5$-Li (or LAH when $R^5$=H) and subsequnetly cyclized to the desired 1-(1H-pyrrol-2-yl)imidazol-2-one.

Synthetic Scheme XXXI shows the preparation of the 1-(1H-imidazol-2-yl)imidazol-2-ones 5 from the corresponding commercially available imidazoles. In Step 1, the imidazole is converted to the N-substituted imidazole under basic conditions. In Step 2, the N-substituted imidazole is metalated and reaacted with carbon dioxide to give the corresponding carboxylic acid. In Step 3, the acid is converted to its corresponding isocyanate via a Curtius rearrangement and reacted in situ with the aminoamide 6 (Scheme IV) to give the urea 8. In Step 4, the urea is reacted with an organolithium

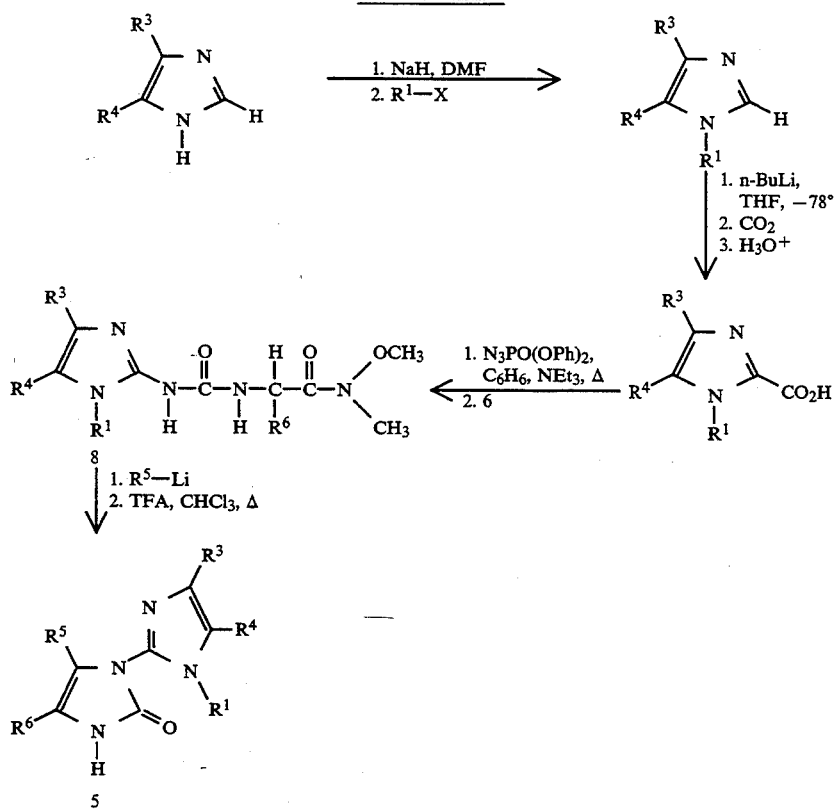

reagent R⁵-Li (or LAH when R⁵=H) and subsequently cyclized to the desired 1-(1H-imidazol-2-yl)imidazol-2-one.

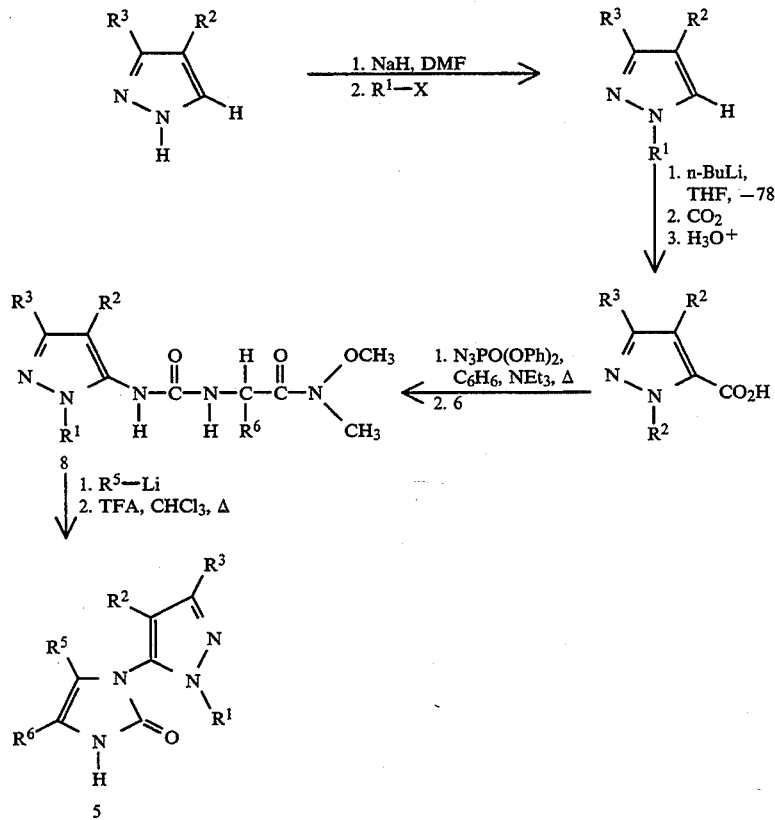

Synthetic Scheme XXXII shows the preparation of the 1-(1H-pyrazol-2-yl)imidazol-2-ones 5 from the corresponding commercially available pyrazoles. In Step 1, the pyrazole is converted to the N-substituted pyrazole under basic conditions. In Step 2, the N-substituted pyrazole is metalated and reacted with carbon dioxide to give the corresponding carboxylic acid. In Step 3, the acid is converted to its corresponding isocyanate via a Curtius rearrangement and reacted in situ with the aminoamide 6 (Scheme IV) to give the urea 8. In Step 4, the urea is reacted with an organolithium reagent R⁵-Li (or LAH when R⁵=H) and subsequently cyclized to the desired 1-(1H-pyrazol-2-yl)imidazol-2-one.

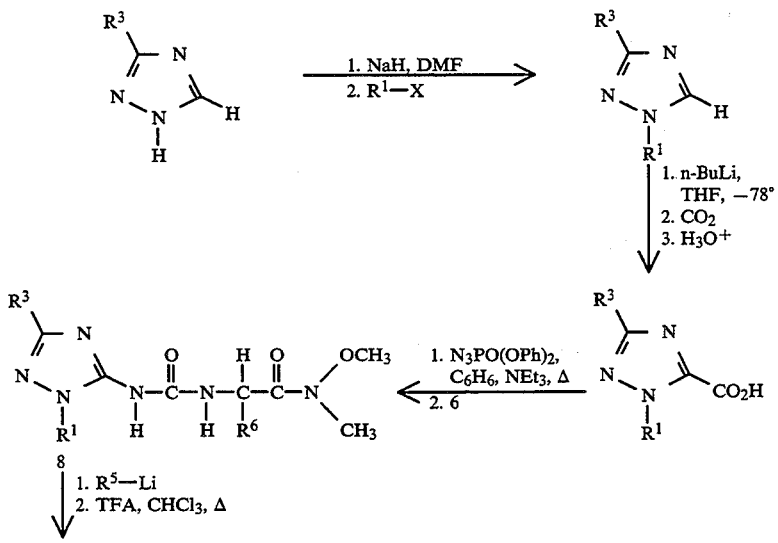

Scheme XXXIII

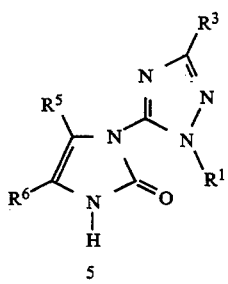

5

Synthetic Scheme XXXIII shows the preparation of the 1-(1H-1,2,4-triazol-5-yl)imidazol-2-ones 5 from the corresponding commercially available 1H-1,2,4-triazoles. In Step 1, the triazole is converted to the N-substituted 1H-1,2,4-triazole under basic conditions. In Step 2, the N-substituted 1H-1,2,4-triazole is metalated and reacted with carbon dioxide to give the corresponding carboxylic acid. In Step 3, the acid is converted to its corresponding isocyanate via a Curtius rearrangement and reacted in situ with the aminoamide 6 (Scheme IV) to give the urea 8. In Step 4, the urea is reacted with an organolithium reagent $R^5$-Li (or LAH when $R^5$=H) and subsequently cyclized to the desired 1-(1H-1,2,4-triazol-5-yl)imidazol-2-one.

Scheme XXXIV

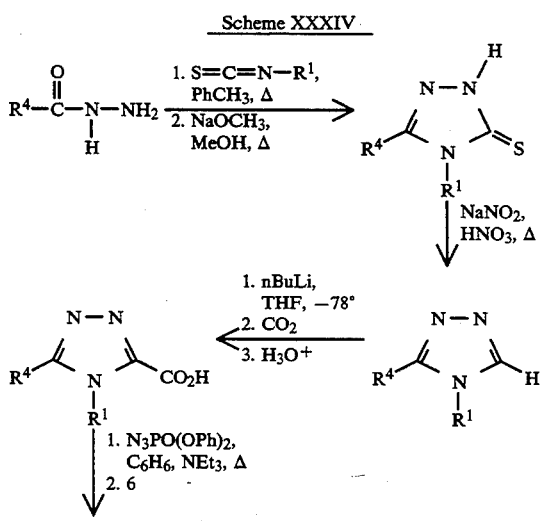

-continued
Scheme XXXIV

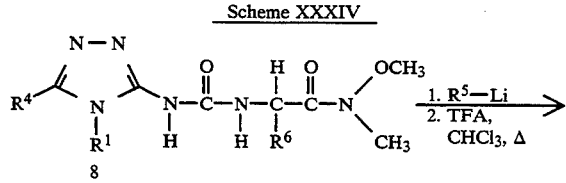

8

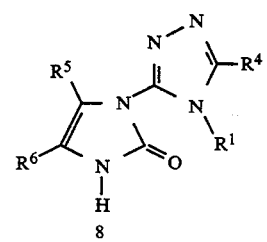

8

Synthetic Scheme XXXIV shows the preparation of the 1-(4H-1,2,4-triazol-3-yl)imidazol-2-ones 5 from the corresponding commercially available hydrazides. In Step 1, the hydrazide is reacted with the appropriate isothiocyanate to give the corresponding $N^2$-acyl-thiosemicarbazide which is subsequently cyclized with sodium methoxide in methanol an reflux to give the 4H-1,2,4-triazol-3-thione. In Step 2, the thione is treated with nitrous acid to give the corresponding reduced 1,2,4-triazole. In Step 3, the N-substituted 4H-1,2,4-triazole is metalated and reacted with carbon dioxide to give the corresponding carboxylic acid. In Step 4, the acid is converted to its corresponding isocyanate via a Curtius rearrangement and reacted in situ with the aminoamide 6 (Scheme IV) to give the urea 8. In Step 5, the urea is reacted with an organolithium reagent $R^5$-Li (or LAH when $R^5$=H) and subsequently cyclized to the desired 1-(4H-1,2,4-triazol-3-yl)imidazol-2-one.

Scheme XXXV

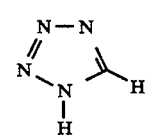

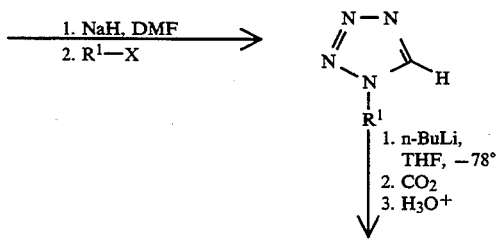

Scheme XXXV

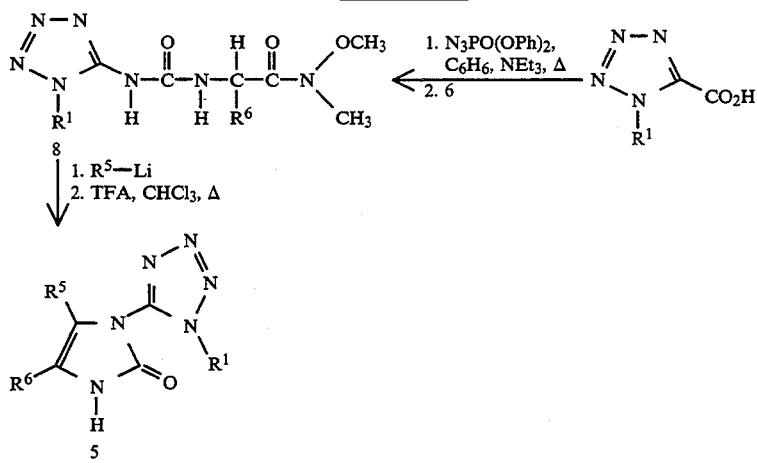

Synthetic Scheme XXXIII shows the preparation of the 1-(1H-tetrazol-5-yl)imidazol-2-ones 5 from the corresponding commercially available 1H-tetrazoles. In Step 1, the tetrazole is converted to the N-substituted 1H-tetrazole under basic conditions. In Step 2, the N-substituted 1H-tetrazole is metalated and reacted with carbon dioxide to give the corresponding carboxylic acid. In Step 3, the acid is converted to its corresponding isocyanate via a Curtius rearrangement and reacted in situ with the aminoamide 6 (Scheme IV) to give the urea 8. In Step 4, the urea is reacted with an organolithium reagent $R^5$-Li (or LAH when $R^5$=H) and subsequently cyclized to the desired 1-(1H-tetrazol-5-yl)imidazol-2-one.

EXAMPLE 1

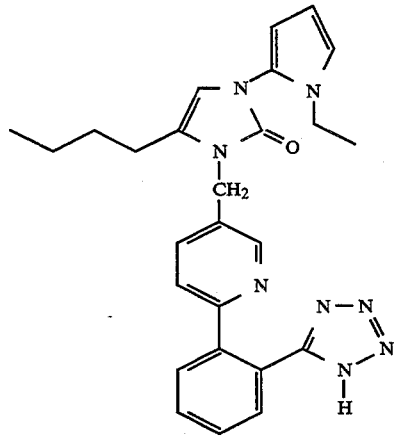

1-(1-ethyl-1H-pyrrol-2-yl)-4-butyl-1,3-dihydro-3-[[6-[2-1H-tetrazol-5-yl)phenyl]-3-pyridinyl]methyl]-2H-imidazol-2-one Step 1: Preparation of N-ethyl pyrrole-2-carboxylic acid Under nitrogen, a suspension of 50 g (0.9 mol) of pulverized KOH in 440 ml of anhydrous DMSO was treated with 20 g (0.18 mol) of pyrrole-2-carboxylic acid (Aldrich); this mixture was cooled in ice and treated with 28 ml (0.36 mol of ethyl iodide. The reaction was allowed to warm to ambient temperatures and stir overnight prior to concentration in vacuo. The residue was dissolved in 125 ml of water and the pH adjusted to 4 with aqueous HCl. The product was extracted with methylene chloride, dried (MgSO$_4$), and concentrated in vacuo to give 19.6 g (78%) of colorless material: mp 77°–78° C.; NMR (DMSO-d$_6$) δ 1.23(t, J=7 Hz, 3H), 4.29(q, J=7 Hz, 2H), 6.06(dd, J=3 and 1 Hz, 1H), 7.10 (t, J=2 Hz, 1H).

Step 2: Preparation of urea

Under nitrogen, 19.78 g (71.9 mmol) of diphenylphosphoryl azide and 10.0 g (71.9 mmol) of N-ethylpyrrole-2-carboxylic acid from Step 1 was dissolved in 300 ml of dry benzene. While stirring, 10.0 ml (7.26 g, 71.9 mmol) of dry triethylamine was added by syringe and the reaction was allowed to stir at reflux for 1 hr. A solution of 12.52 (71.9 mmol) of the free aminoamide 6 (generated by treating the TFA salt with Na$_2$CO$_3$, continuously extracting with ether overnight, drying (MgSO$_4$), and concentrating in vacuo) in 60 ml of benzene was added rapidly and the reaction was allowed to stir at reflux for an additional 6 hrs. The benzene was removed in vacuo and the residue dissoved in 600 ml of ethyl acetate which was washed twice with 200 ml of 1M Na$_2$CO$_3$, 200 ml of water, 100 ml of brine, and dried (MgSO$_4$). Concentration in vacuo gave 20.6 g (92%) of amide product. Purification by silica gel chromatography (Water Prep 500A) using ethyl acetate/methylene chloride (1:1) gave 14.2 g (64%) of pure urea as an oil: NMR (CDCl$_3$) δ 0.67 (t, J=7 Hz, 3H), 1.01–1.19 (m, 5H), 1.21–1.34 (m, 2H), 1.40–1.55 (m, 2H), 2.97 (s, 3H), 3.58 (s, 3H), 3.65 (q, J=7 Hz, 2H), 4.61–4.72 (m, 1H), 5.22 (br d, 1H), 5.81 (br s, 1H), 5.83–5.87 (m, 1H), 5.91 (t, J=3 Hz, 1H), 6.42 (t, J=2 Hz, 1H ).

Step 3: Preparation of 1-(1-ethyl-1H-pyrrol-2-yl)-4-butyl-1,3-dihydro-2H-imidazol-2-one Under nitrogen, 3.30 g (10.6 mmol) of the urea from Step 2 was dissolved in 50 ml of anhydrous ether and slowly treated with 6.9 mmol of LAH in ether. After 4 hrs, 50 ml of water was slowly added and the layers separated. The aqueous layer was extracted with ether and the organic layer and ether extracts were combined and dried (MgSO$_4$). Concentration in vacuo gave 2.0 g (81%) of 1-(1-ethyl-1H-pyrrol-2-yl)-4-butyl-1,3-dihydro-2H-imidazol-2-one as a yellow pale oil: NMR (CDCl$_3$) δ 0.98(t, J=8 Hz, 3H), 1.24–1.42 (m, 2H), 1.32 (t, J=8 Hz, 3H), 1.44–1.57 (m, 2H), 2.34 (t, J=8 Hz, 2H), 3.79 (q, J=8 Hz, 2H), 5.90 (br s, 1H), 6.05 (dd, J=3 and 2 Hz, 1H), 6.13 (t, J=3 Hz, 1H), 6.62 (t, J=2 Hz, 1H).

Step 4: Preparation of 1-(1-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one.

Under nitrogen, a solution of 6.9 mmol of the imidazol-2-one from Step 3 in 50 ml of anhydrous DMF was cooled to −60° C. and treated with 6.9 mmol of potassium tertbutoxide in THF. To this was added a solution of 6.3 mmol of 53 [Scheme XXII], $R^7=CN_4C(C_6H_5)_3$], 2.7 mmol of tetrabutylammonium iodide, and 3.6 mmol of potassium iodide in 15 ml of anhydrous DMF. The reaction was allowed to slowly warm to ambient temperature overnight and concentrated in vacuo. The residue was dissolved in methylene chloride, washed with water, dried (MgSO$_4$), and reconcentrated. Purification by silica gel chromatography (Waters Prep 500A) using ethyl acetate/methylene chloride (3:7) gave 1.92 g (43% of protected coupled product. This material was dissolved in acetic acid/water (9:1) and stirred overnight at ambient temperature. The solvent was removed in vacuo; the residue was dissolved dilute base, washed several times with ether to remove triphenylmethylcarbinol, and acidified to pH 4 with dilute HCl. This solution was then extracted several times with ethyl acetate, dried (MgSO$_4$), and reconcentrated. Recrystallization from acetonitrile gave 528 mg (46%) of 1-(1-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one as a colorless solid: mp 174°–175° C.; NMR (CDCl$_3$) δ 0.88 (t, J=8 Hz, 3H), 1.29–1.43 (m, 2H), 1.34 (t, J=7 Hz, 3H), 1.44–1.56 (m, 2H), 2.32 (t, J=8 Hz, 2H), 3.80 (q, J=8 Hz, 2H), 5.04 (s, 2H), 6.05 (s, 1H), 6.08–6.12 (m, 1H), 6.14 (t, J=3 Hz, 1H), 6.65 (t, J=2 Hz, 1H), 7.23 (d, J=9 Hz, 1H), 7.41–7.54 (m, 3H), 7.65 (dd, J=9 and 2 Hz, 1H), 7.91–7.98 (m, 1H), 8.52 (d, J=2 Hz, 1H); MS(FAB)m/e (rel intensity) 469 (26), 441 (12), 232 (14), 209 (100), 194 (29), 180 (58), 152 (9); HRMS. Calc'd for M+H: 469.2464. Found: 469.2500.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 105 cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C, between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded (3×10$^{-10}$ to 1×10$^{-5}$M). Each concentration of AII was allowed to elicit its maximal contraction, and then AII was washed out repeatedly for 30 minutes before rechallenging with a higher concentration of AII. Aorta rings were exposed to the test antagonist at 10$^{-5}$ M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol. Chemother.*, 2, 189–206 (1947)]. The pA$_2$ value is the concentration of the antagonist which increases the EC$_{50}$ value for AII by a factor of two. Each test antagonist was evaluated in aorta rings from two rabbits. Results are reported in Table I.

Assay C: In Vivo Intragastric Pressor Assay Response for All Antagonists

Male Sprague-Dawley rats weighing 225–300 grams were anesthetized with methohexital (30 mg/kg, i.p.) and catheters were implanted into the femoral artery and vein. The catheters were tunneled subcutaneously to exit dorsally, posterior to the head and between the scapulae. The catheters were filled with heparin (1000 units/ml of saline). The rats were returned to their cage and allowed regular rat chow and water ad libitum. After full recovery from surgery (3–4 days), rats were placed in Lucite holders and the arterial line was connected to a pressure transducer. Arterial pressure was recorded on a Gould polygraph (mmHg). Angiotensin II was administered as a 30 ng/kg bolus via the venous catheter delivered in a 50 μl volume with a 0.2 ml saline flush. The pressor response in mm Hg was measured by the difference from pre-injection arterial pressure to the maximum pressure achieved. The AII injection was repeated every 10 minutes until three consecutive injections yielded responses within 4 mmHg of each other. These three responses were then averaged and represented the control response to AII. The test compound was suspended in 0.5% methylcellulose in water and was administered by gavage. The volume administered was 2 ml/kg body weight. The standard dose was 3 mg/kg. Angiotensin II bolus injections were given at 30, 45, 60, 75, 120, 150, and 180 minutes after gavage. The pressor response to AII was measured at each time point. The rats were then returned to their cage for future testing. A minimum of 3 days was allowed between tests. Percent inhibition was calculated for each time point following gavage by the following formula: [(Control Response—Response at time point)/Control Response]×100. Results are shown in Table I.

TABLE I

In Vitro and In Vivo Angiotensin II Activity of Compounds of the Invention

| Test Compound Example # | [1]Assay A $IC_{50}$ (nM) | [2]Assay B $pA_2$ | [3]Assay C Dose: 3 mg/kg (i.g.) | |
|---|---|---|---|---|
| | | | Inhibition (%) | Duration (min.) |
| 1 | 1.7 | NT | 15 | >180 |

[1]Assay A: Angiotensin II Receptor Binding Activity
[2]Assay B: In Vitro Vascular Smooth Muscle Response
[3]Assay C: In Vivo Pressor Response (all test compounds administered intragastrically at 3 mg/kg).
NT = Not Tested Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intra-vascularly, intraperitoneally, subcutaneously, intra-muscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method for treating a glaucoma disorder related to elevated intraocular pressure, which elevated intraocular pressure is mediated by action of an angiotensin II receptor antagonist, said method comprising administering to a subject susceptible to or afflicted with such glaucoma disorder a therapeutically-effective amount of an angiotensin II receptor antagonist compound of Formula I:

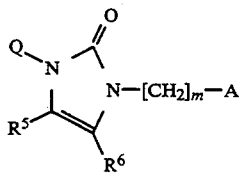

wherein Q is a heterocyclic group having five ring-member atoms, which ring-member atoms are selected from carbon atoms and nitrogen atoms, with the requirement that at least one ring-member atom be a carbon atom and at least one ring member atom be a nitrogen atom, which heterocyclic group is fully unsaturated and wherein said heterocyclic group may be substituted on one or more substitutable positions by one or more groups independently selected from hydrido, alkyl, alkoxy, cyano, halo, hydroxy, nitro, amino, alkylamino, carboxyl, alkoxycarbonyl, formyl, oxo, alkylcarbonyl and haloalkylcarbonyl; wherein $R^5$ is selected from hydrido, alkyl, halo, haloalkyl, formyl, carboxyl and alkoxyalkyl; wherein $R^6$ is selected from alkyl, phenyl, phenylalkyl, cycloalkyl and cycloalkylalkyl; wherein A is an acid-group-substituted pyridinyl-phenyl moiety selected from

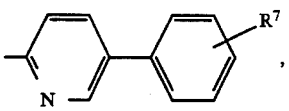

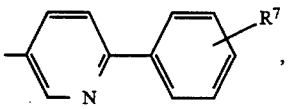

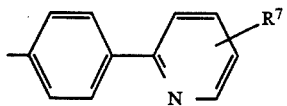

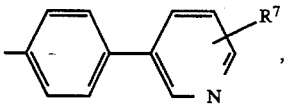

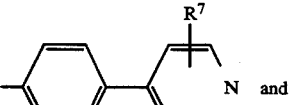

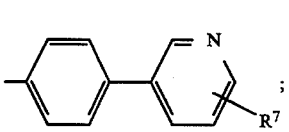

wherein m is a number selected from one to four, inclusive; wherein $R^7$ is an acidic group selected from COOH and

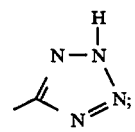

or a stereoisomer or a tautomer thereof or a pharmaceutically-acceptable salt thereof.

2. The method of claim 1 wherein Q is selected from the group of moieties consisting of:

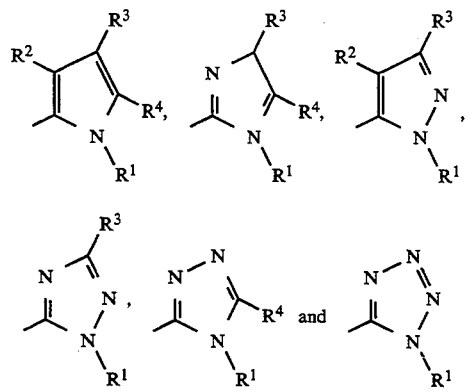

wherein $R^1$ is selected from hydrido and alkyl; wherein each $R^2$, $R^3$ and $R^4$ is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein $R^5$ is selected from hydrido, methyl, fluoro, chloro, monofluoromethyl, difluoromethyl, trifluoromethyl, formyl, carboxyl and dimethoxymethyl; wherein $R^6$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

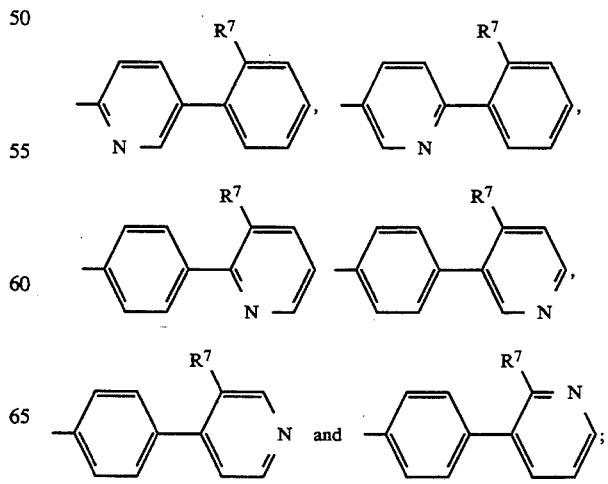

wherein R[7] is an acidic group selected from COOH and

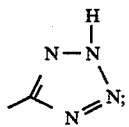

or a stereoisomer or a tautomer thereof or a pharmaceutically-acceptable salt thereof.

3. The method of claim 2 wherein said angiotensin II receptor antagonist compound is of Formula II:

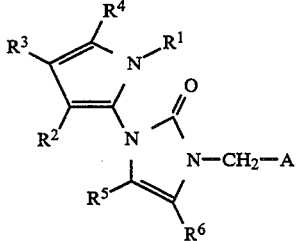

II wherein R[1] is selected from hydrido and alkyl; wherein each R[2], R[3] and R[4] is independently selected from hydrido, methyl, ethyl, n-propyl, isopropyl, tert-butyl, methoxy, ethoxy, propoxy, isopropoxy, tert-butoxy, cyano, fluoro, chloro, iodo, bromo, hydroxy, nitro, amino, N-methylamino, N,N-dimethylamino, N-ethylamino, N,N-diethylamino, carboxyl, methoxycarbonyl, ethoxycarbonyl, formyl, methylcarbonyl, ethylcarbonyl and trifluoromethylcarbonyl; wherein R[5] is selected from hydrido, methyl, fluoro, chloro, monofluoromethyl, difluoromethyl, trifluoromethyl, formyl, carboxyl and dimethoxymethyl; wherein R[6] is selected from methyl, ethyl, n-propyl, isopropyl, n-butyl, sec-butyl, isobutyl, tert-butyl, n-pentyl, isopentyl, neopentyl, phenyl, benzyl, phenethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl and cyclohexylethyl; wherein A is an acidic-group-substituted pyridinyl-phenyl moiety selected from

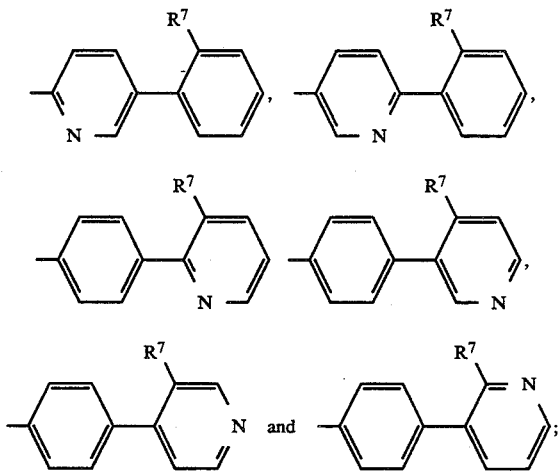

wherein R[7] is an acidic group selected from COOH and

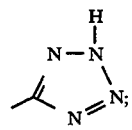

or a stereoisomer or a tautomer thereof or a pharmaceutically-acceptable salt thereof.

4. The method of claim 3 wherein said angiotensin II receptor antagonist compound is of Formula II(b):

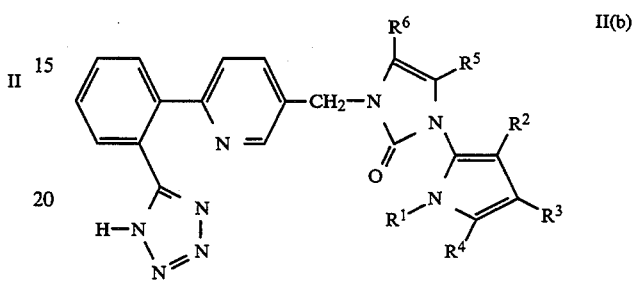

II(b)

wherein R[1] is selected from hydrido, methyl, ethyl, n-propyl, isopropyl, n-butyl, tert-butyl, sec-butyl, isobutyl and n-pentyl; wherein R[2], R[3] and R[4] may be independently selected from hydrido, methyl, ethyl, n-propyl, isopropyl, tert-butyl, hydroxy, methoxy, fluoro, chloro, iodo, bromo, carboxyl, formyl, methylcarbonyl and trifluoromethylcarbonyl; wherein R[5] is hydrido; wherein R[6] is selected from methyl, ethyl, n-propyl, isopropyl, n-butyl, sec-butyl, isobutyl, tert-butyl, n-pentyl, isopentyl and neopentyl; or a stereoisomer or a tautomer thereof or a pharmaceutically-acceptable salt thereof.

5. The method of claim 4 wherein said angiotensin II receptor antagonist compound is selected from compounds and their stereoisomers and tautomers and the pharmaceutically-acceptable salts thereof, said compounds consisting of 1-(1-methyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-ethyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-propyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-isopropyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-butyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-( 1-secbutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-isobutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1-(1-tertbutyl-1H-pyrrol-2-yl)-4-propyl-1,3-dihydro-3-[[6-[2-(1H-tetrazol-5-yl)phenyl]-3-pyridinyl]methyl]-2H-imidazol-2-one;

1(1-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-butyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-secbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isobutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-dimethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-methyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-diethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-ethyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3-dipropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-isopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-( 1-propyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-( 1-propyl-3-hydroxymethyl-1H-pyrrol-2-yl)-4-butyl-1,3-dihydro-3-[[6-[2 -(1H-tetrazol-5-yl)phenyl]-3-pyridinyl]methyl]-2H-imidazol-2-one;

1-(1-propyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-fluoro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-cyano-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-propyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-methyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-ethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-propyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1,3 -diisopropyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-trifluoromethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-hydroxymethyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-carbomethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-carboxy-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-acetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-trifluoroacetyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-chloro-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-formyl-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-bromo-1H-pyrrol-2-yl)-4-butyl-1,3-dihydro-3-[[6-[2-(1H-tetrazol-5-yl)phenyl]-3-pyridinyl]methyl]-2H-imidazol-2-one;

1-(1-isopropyl-3-fluoro-1H-pyrrol-2-yl)-4-butyl-1,3-dihydro-3-[[6-[2-(1H-tetrazol-5)phenyl]-3-pyridinyl]methyl]-2H-imidazol-2-one;

1-(1-isopropyl-3-cyano-1H-pyrrol-2-yl)-4-butyl-1,3-dihydro-3-[[6-[2-(1H-tetrazol-5)phenyl]-3-pyridinyl]methyl]-2H-imidazol-2-one;

1-(1-isopropyl-3-carboethoxy-1H-pyrrol-2-yl)-4-butyl-1,3-dihydro-3-[[6-[2-(1H-tetrazol-5-yl)phenyl]-3-pyridinyl]methyl]-2H-imidazol-2-one and 1-(1-isopropyl-3-tertbutyl-1H-pyrrol-2-yl)-4-butyl-1,3-dihydro-3-[[6-[2-(1H-tetrazol-5-yl)phenyl]-3-pyridinyl]methyl]-2H-imidazol-2-one.

6. The method of claim 5 wherein said angiotensin II receptor antagonist compound is 1-(1-ethyl-1H-pyrrol-2yl)-4-butyl-1,3-dihydro-3-[[6-[2-((1H-tetrazol-5-yl)phenyl]-3-pyridinyl]methyl]-2H-imidazol-2-one or a pharmaceutically-acceptable salt thereof.

* * * * *